United States Patent
Benner

(10) Patent No.: US 8,053,212 B1
(45) Date of Patent: Nov. 8, 2011

(54) NON-STANDARD NUCLEOSIDE ANALOGS WITH REDUCED EPIMERIZATION

(76) Inventor: Steven Albert Benner, Gainesville, FL (US)

( * ) Notice: Subject to any disclaimer, the term of this patent is extended or adjusted under 35 U.S.C. 154(b) by 782 days.

(21) Appl. No.: 11/372,400

(22) Filed: Mar. 9, 2006

Related U.S. Application Data

(63) Continuation of application No. 11/212,230, filed on Aug. 27, 2005, now abandoned.

(60) Provisional application No. 60/617,636, filed on Oct. 13, 2004, provisional application No. 60/614,413, filed on Sep. 29, 2004, provisional application No. 60/605,061, filed on Aug. 28, 2004.

(51) Int. Cl.
| | |
|---|---|
| *C12P 19/34* | (2006.01) |
| *C07H 19/00* | (2006.01) |
| *C07H 19/048* | (2006.01) |
| *C07H 5/06* | (2006.01) |
| *C07D 213/44* | (2006.01) |
| *C07D 213/00* | (2006.01) |

(52) U.S. Cl. .................. 435/91.1; 536/27.11; 536/28.1; 536/29.2; 546/262; 546/264

(58) Field of Classification Search ................ None
See application file for complete search history.

(56) References Cited

U.S. PATENT DOCUMENTS

| | | | | |
|---|---|---|---|---|
| 5,432,272 | A | * | 7/1995 | Benner ........................ 536/25.3 |
| 6,140,496 | A | * | 10/2000 | Benner ........................ 536/27.1 |

OTHER PUBLICATIONS

Hutter and Benner, "Expanding the Genetic Alphabet: Non-Epimerizing Nucleoside with the pyDDA Hydrogen Bonding Pattern," Journal of Organic Chemistry, 68(25), 9839-9842 (2003); Web publ. Nov. 13, 2003).*

Yang et al., "Artificially Expanded Genetic Information System: A New Base Pair with Alternative Hydrogen Bonding Pattern," Nucleic Acids Research, 34(21), 6095-6101 (2006); Web publ. Oct. 29, 2006).*

Watanabe et al., "Novel Ring Transformation Reactions and Their Applications to the Synthesis of Potential Anticancer Heterocyclic Compounds," Heterocycles. 21(1), 289-307 (1984).*

Sheng, P. P., Yang, Z. Y., Kim, Y. M., Wu, Y. R., Tan, W. H. Benner, S. A. (2008) Design of a novel molecular beacon. Modification of the stem with artificially genetic alphabet. Chem. Comm. (41), 5128-5130.

Yang, Z., Hutter, D., Sheng, P., Sismour, A. M., Benner, S. A. (2006) Artificially expanded genetic information system: A new base pair with an alternative hydrogen bonding pattern. Nucl. Acids Res. 34, 6095-6101.

Yang, Z., Sismour, A. M., Sheng, P., Puskar, N. L., Benner, S. A. (2007) Enzymatic incorporation of a third nucleobase pair. Nucl. Acids Res. 35, 4238-4249.

Yang, Z., Chen, F., Chamberlin, S. G., Benner, S. A. (2010) Expanded genetic alphabets in the polymerase chain reaction. Angew. Chem. 49, 177-180.

Robbins, D.J., Barkley, M.D., Coleman, M.S. (1987) Interaction of terminal transferase with single-stranded DNA. J of Biol.Chem. 262, 9494-9502.

von Krosigk, U., Benner, S. A. (1995) pH-independent triple helix formation by an oligonucleotide containing a pyrazine donor-donor-acceptor base. J. Am. Chem. Soc. 117, 5361-5362.

Voegel, J. J., Benner, S. A. (1994) Non-standard hydrogen bonding in duplex oligonucleotides. The base pair between an acceptor-donor-donor pyrimidine analog and a donor-acceptor-acceptor purine analog. J. Am. Chem. Soc. 116, 6929-6930.

* cited by examiner

*Primary Examiner* — Lawrence E Crane

(57) ABSTRACT

This invention relates to nucleoside, nucleotide, and oligonucleotide analogs that incorporate non-standard nucleobase analogs, defined to be those that present a pattern of hydrogen bonds to a paired nucleobase analog in a complementary strand that is different from the pattern presented by adenine, guanine, cytosine, and thymine. The invention is specifically concerned with compositions of matter that present the donor-donor-acceptor, donor-acceptor-donor, and acceptor-donor-donor non-standard hydrogen bonding patterns on pyrimidine analogs, where nucleoside analogs bearing these pyrimidine analogs do not epimerize as easily as those known in the art. The heterocycles on these nucleoside analogs are diaminopyridines and aminopyridones that have electron withdrawing groups attached to the position analogous to the 5-position of the ring in standard pyrimidines, including nitro, cyano, and carboxylic acid derivatives.

16 Claims, 18 Drawing Sheets

R as typically been H or alkyl

X = CH or N = 4

X = CH, or N

W = an electron withdrawing group
-NO₂
-CN
-CC-CN
-CH=CH-CN
-CC-COOR
-CH=CH-COOR
-CC-CONHR
-CH=CH-CONHR R = sugar, W = electron withdrawing group a) NIS, DMF a) 1. Pd(OAc)$_2$, AsPh$_3$, Bu$_3$N, DMF, Ar, 60°C

NON-STANDARD NUCLEOSIDE ANALOGS WITH REDUCED EPIMERIZATION

CROSS REFERENCE TO RELATED APPLICATIONS

This application is a continuation of Ser. No. 11/212,230 filed 27 Aug. 2005, now abandoned, which claimed the priority of U.S. provisional applications 60/605,061 filed 28 Aug. 2004, 60/614,413, filed 29 Sep. 2004, and 60/617,636, filed 13 Oct. 2004.

STATEMENT OF RIGHTS TO INVENTIONS MADE UNDER FEDERALLY-SPONSORED RESEARCH

This invention was made with government support under GM54048 awarded by NIH. The government has certain rights in the invention.

FIELD OF INVENTION

This invention relates to the field of nucleic acid chemistry, more specifically to the field of nucleic acid analogs, and most specifically to oligonucleotide analogs that incorporate non-standard nucleobases, those that present to a complementary strand in a Watson-Crick pairing geometry a pattern of hydrogen bonds that is different from the pattern presented by adenine, guanine, cytosine, and thymine. Most specifically, this invention discloses and claims compositions of matter that present the donor-donor-acceptor, donor-acceptor-donor, and acceptor-donor-donor non-standard hydrogen bonding patterns on pyrimidine nucleoside analogs that do not epimerize as easily as those known in the prior art.

BACKGROUND

Natural oligonucleotides bind to complementary oligonucleotides according to the well-known rules of nucleobase pairing first elaborated by Watson and Crick in 1953, where adenine (A) pairs with thymine (T) (or uracil, U, in RNA), and guanine (G) pairs with cytosine (C), with the complementary strands anti-parallel to one another. In this disclosure, "DNA" or "nucleic acid" is understood to include, as appropriate, both DNA (where the sugar is 2'-deoxyribose) and RNA (where the sugar is ribose), as well as derivatives where the sugar is modified, as in 2'—O-methyl, 2'-O-allyl, 2'-deoxy-2'-fluoro, and 2',3'-dideoxynucleoside derivatives, nucleic acid analogs based on other sugar backbones, such as threose, locked nucleic acid derivatives, bicyclo sugars, or hexose, glycerol and glycol sugars [Zhang, L., Peritz, A., Meggers, E. (2005) A simple glycol nucleic acid. *J. Am. Chem. Soc.* 127, 4174-4175], nucleic acid analogs based on non-ionic backbones, such as "peptide nucleic acids", these nucleic acids and their analogs in non-linear topologies, including as dendrimers, comb-structures, and nanostructures, and these nucleic acids and their analogs carrying tags (e.g., fluorescent, functionalized, or binding) to the ends, sugars, or nucleobases.

These pairing rules allow for the specific hybridization of an oligonucleotide to a complementary oligonucleotide, making oligonucleotides valuable as probes in the laboratory, in diagnostic applications, as messages that can direct the synthesis of specific proteins, and in a wide range of other applications well known in the art. Such base pairing is used, for examples and without limitation, to capture other oligonucleotides to beads, arrays, and other solid supports, to allow nucleic acids to fold in hairpins, beacons, and catalysts, as supports for functionality, such as fluorescence, fluorescence quenching, binding/capture tags, and catalytic functionality, as part of more complex architectures, including dendrimers and nanostructures, and as scaffolds to guide chemical reactions.

Further, nucleobase pairing is the basis by which enzymes are able to catalyze the synthesis of new oligonucleotides that are complementary to template nucleotides. In this synthesis, building blocks (normally the triphosphates of ribo- or deoxyribonucleosides carrying of A, T, U, C, or G) are directed by a template oligonucleotide to form a complementary oligonucleotide with the complementary sequence. This process is the basis for replication of all forms of life, and also serves as the basis for technologies for enzymatic synthesis and amplification of specific heterosequence nucleic acids by enzymes such as DNA and RNA polymerase, in the polymerase chain reaction (PCR), and in a variety of architectures that may involve synthesis, ligation, cleavage, immobilization and release, inter alia, used in technology to detect nucleic acids.

Nucleobase pairing following rules of complementarity is known to be useful in a variety of architectures. In solution, nucleobase pairing in the loop of a molecular beacon can open the beacon, separating a fluorescent species attached to one end of a hairpin structure from a quencher on the other. Pairing can assemble two DNA fragments transiently or covalently, as in a template-directed ligation. Pairing is useful for affixing an oligonucleotide that is free in solution to a support carrying the complementary oligonucleotide. The oligonucleotide can carry functional groups, including fluorescent groups attached to the nucleobases.

The Watson-Crick pairing rules can be understood chemically in terms of the arrangement of hydrogen bonding groups on the heterocyclic nucleobases of the oligonucleotide, groups that can either be hydrogen bond donors or acceptors. In the standard Watson-Crick geometry, a large purine nucleobase pairs with a small pyrimidine nucleobase. Thus, the AT nucleobase pair is the same size as a GC nucleobase pair. This means that the rungs of the DNA ladder, formed from either AT or GC nucleobase pairs, all have the same length.

Further recognition between nucleobases is determined by hydrogen bonds between the nucleobases. In standard nucleobases, hydrogen bond donors are heteroatoms (nitrogen or oxygen in the natural nucleobases) bearing a hydrogen; hydrogen bond acceptors are heteroatoms (nitrogen or oxygen in the natural nucleobases) with a lone pair of electrons. In the geometry of the Watson-Crick nucleobase pair, a six membered ring (in standard nucleobases, a pyrimidine) is juxtaposed to a ring system composed of a fused six membered ring and a five membered ring (in standard nucleobases, a purine), with a middle hydrogen bond linking two ring atoms, and hydrogen bonds on either side joining functional groups appended to each of the rings, with donor groups paired with acceptor groups.

In many applications, the nucleobases incorporated into one or more oligonucleotide analogs carry an appendage. In standard nucleobases, the appendage, or side chain, is attached to one or more pyrimidines at the 5-position, or at the 7-position of a 7-deazapurine, or to an exocyclic nitrogen, most often the exocyclic amino group of adenine or cytosine. Such nucleoside analogs have application because of their combination of Watson-Crick nucleobase pairing ability and the properties or reactivities associated with species appended via the side chain. For example, oligonucleotides containing a T to which is appended a side chain bearing a biotin residue can first bind to a complementary oligonucleotide, and the hybrid can then be isolated by virtue of the specific affinity of biotin to avidin [Langer, P. R.; Waldrop, A. A.; Ward, D. C. (1981) *Proc. Nat. Aced. Sci.* 78, 6633-6637]. This finds application in diagnostic work. Instead of biotin, the side chain can carry a fluorescent moiety, or a moiety that quenches the fluorescence of another moiety, a branching point, or a moiety that complexes to a metal, or a moiety that confers catalytic activity on the oligonucleotide, or a moiety that assists in the attachment of the oligonucleotide analog to a solid support, such as a bead, a one dimensional array, or a two dimensional array.

Often, derivatized standard nucleotides can be incorporated into oligonucleotides by enzymatic transcription of natural oligonucleotide templates in the presence of the triphosphate of the derivatized nucleoside, the substrate of the appropriate (DNA or RNA) polymerase, or a reverse transcriptase. In this process, a natural nucleoside is placed in the template, and standard Watson-Crick nucleobase pairing is exploited to direct the incoming modified nucleoside opposite to it in the growing oligonucleotide chain.

The standard available nucleobase pairs are limited in that they make available only two mutually exclusive hydrogen bonding patterns. This means that should one wish to introduce a modified nucleoside based on one of the natural nucleosides into an oligonucleotide, it would be incorporated wherever the complementary natural nucleoside is found in the template. For many applications, this is undesirable.

Further, in many applications, it would be desirable to have nucleobase pairs that behave as predictably as the AT (or U) and GC nucleobase pairs, but that do not cross-pair with natural oligonucleotides, which are built from A, T (or U), G, and C. This is especially true in diagnostics assays based. Biological samples generally contain many nucleic acid molecules in addition to the nucleic acid that one wishes to detect. The adventitious DNA/RNA, often present in abundance over the targeted analyte DNA (or RNA), is also composed of A, T (or U), G, and C. Thus, adventitious DNA/RNA can compete with the desired interactions between two or more oligonucleotide-like molecules.

Many of the limitations that arise from the existence of only four standard nucleobases, joined in only two types of nucleobase pairs via only two types of hydrogen bonding schemes, could be overcome were additional nucleobases available that could be incorporated into oligonucleotides. Here, the additional nucleobases would still pair in the Watson-Crick geometry, but would present patterns of hydrogen bond donating and accepting groups in a pattern different from those presented by the natural nucleobases. They therefore would form nucleobase pairs with additional complementary nucleobases in preference to (and, preferably, with strong preference to, meaning with at least a 10 to 100 fold affinity greater than to mismatched oligonucleotides or oligonucleotide analogs). In the last decade, Benner disclosed compositions of matter that were intended to overcome the limitations of molecular recognition by changing the pattern of hydrogen bond donor and acceptor groups presented by a nucleobase to the nucleobase on a complementary oligonucleotide analog [U.S. Pat. Nos. 5,432,272, 5,965,364, 6,001,983, 6,037,120, 6,140,496, 6,627,456, 6,617,106]. These disclosures showed that the geometry of the Watson-Crick nucleobase pair can accommodate as many as 12 nucleobases forming 6 mutually exclusive pairs. Of these, four nucleobases forming two pairs are "standard", while eight nucleobases forming four pairs were termed "non-standard". Adding the non-standard nucleobases to the standard nucleobases yielded an Artificially Expanded Genetic Information System (AEGIS). Specifically, the structures shown in FIG. 1, taken from U.S. Pat. No. 6,140,496, implement the designated hydrogen bonding patterns. It was also noted that these nucleobases analogs might be functionalized to enable a single biopolymer capable of both genetics and catalysis. Expanded genetic alphabets have now been further explored in a variety of laboratories, and the possibility of a fully artificial genetic system has been advanced [Switzer, C. Y., Moroney, S. E., Benner, S. A. (1989) Enzymatic incorporation of a new base pair into DNA and RNA. *J. Am. Chem. Soc.* 111, 8322-8323][Piccirilli, J. A., Krauch, T., Moroney, S. E., Benner, S. A. (1990) Extending the genetic alphabet. Enzymatic incorporation of a new base pair into DNA and RNA. *Nature* 343, 33-37][Piccirilli, J. A., Krauch, I., MacPherson, L. J., Benner, S. A. (1991) A direct route to 3-(ribofuranosyl)-pyridine nucleosides. *Helv. Chim. Acta* 74, 397-406] [Voegel, J. J., Altorfer, M. M., Benner, S. A. (1993) The donor-acceptor-acceptor purine analog. Transformation of 5-aza-7-deaza-isoguanine to 2'-deoxy-5-aza-7-deaza-iso-guanosine using purine nucleoside phosphorylase. *Helv. Chim Acta* 76, 2061-2069] [Voegel, J. J., von Krosigk, U., Benner, S. A. (1993) Synthesis and tautomeric equilibrium of 6-amino-5-benzyl-3-methylpyrazin-2-one. An acceptor-donor-donor nucleoside base analog. *J. Org. Chem.* 58, 7542-7547][Heeb, N. V., Benner, S. A. (1994) Guanosine derivatives bearing an $N^2$-3-imidazolepropionic acid. *Tetrahedron Lett.* 35, 3045-3048] [Voegel, J. J., Benner, S. A. (1994) Non-standard hydrogen bonding in duplex oligonucleotides. The base pair between an acceptor-donor-donor pyrimidine analog and a donor-acceptor-acceptor purine analog. *J. Am. Chem. Soc.* 116, 6929-6930][von Krosigk, U., Benner, S. A. (1995) pH-independent triple helix formation by an oligonucleotide containing a pyrazine donor-donor-acceptor base. *J. Am. Chem. Soc.* 117, 5361-5362][Voegel, J. J., Benner, S. A. (1996) Synthesis, molecular recognition and enzymology of oligonucleotides containing the non-standard base pair between 5-aza-7-deaza-iso-guanine and 6-amino-3-methylpyrazin-2-one, a donor-acceptor-acceptor purine analog and an acceptor-donor-donor pyrimidine analog. *Helv. Chim. Acta* 79, 1881-1898] [Voegel, J. J., Benner, S. A. (1996) Synthesis and characterization of non-standard nucleosides and nucleotides bearing the acceptor-donor-donor pyrimidine analog 6-amino-3-methylpyrazin-2-one. *Helv. Chim. Acta* 79, 1863-1880][Kodra, J., Benner, S. A. (1997) Synthesis of an N-alkyl derivative of 2'-deoxyisoguanosine. *Syn. Lett.,* 939-940] [Jurczyk, S., Kodra, J. T., Rozzell, J. D., Jr., Benner, S. A., Battersby, T. R. (1998) Synthesis of oligonucleotides containing 2'-deoxyisoguanosine and 2'-deoxy-5-methyliso-cytidine using phosphoramidite chemistry. *Helv. Chim. Acta* 81, 793-811][Lutz, S., Burgstaller, P., Benner, S. A. (1999) An in vitro screening technique for polymerases that can incorporate modified nucleotides. Pseudouridine as a substrate for thermostable polymerases. *Nucl. Acids Res.* 27, 2792-2798][Jurczyk, S. C., Battersby, T. R., Kodra, J. T., Park, J.-H., Benner, S. A. (1999) Synthesis of 2'-deoxyisoguanosine triphosphate and 2'-deoxy-5-methyl-isocytidine triphosphate. *Helv. Chim. Acta.* 82, 1005-1015] [Jurczyk, S. C., Horlacher, J., Devine, K. G., Benner, S. A., Battersby, I. R. (2000) Synthesis and characterization of oligonucleotides containing 2'-deoxyxanthosine using phosphoramidite chemistry. *Helv. Chim. Acta* 83, 1517-1524][Rao, P., Benner, S. A. (2001) A fluorescent charge-neutral analog of xanthosine: Synthesis of a 2'-deoxyribonucleoside bearing a 5-aza-7-deazaxanthine base. *J. Org. Chem.* 66, 5012-50151.

To systematize the nomenclature for the hydrogen bonding patterns, the hydrogen bonding pattern implemented on a small component of a nucleobase pair pare designated by the prefix "py". Following this prefix is the order, from the major groove to the minor groove, of hydrogen bond acceptor (A) and donor (D) groups. Thus, both thymine and uracil implement the standard hydrogen bonding pattern pyADA. The standard nucleobase cytosine implements the standard hydrogen bonding pattern pyDAA. Hydrogen bonding patterns implemented on the large component of the nucleobase pair are designated by the prefix "pu". Again following the prefix, the hydrogen bond donor and acceptor groups are designated, from the major to the minor grooves, using "A" and "D". Thus, the standard nucleobases adenine and guanine implement the standard hydrogen bonding patterns puDA- and puADD respectively.

A central teaching of this disclosure is that hydrogen bonding pattern designated using this systematic nomenclature is distinct, in concept, from the organic molecule that is used to implement the hydrogen bonding pattern. Thus, guanosine is a nucleoside that implements the puADD hydrogen bonding pattern. So does, however, 7-deazaguanosine, 3-deazaguanosine, 3,7-dideazaguanosine, and any of any number of other purines and purine derivatives, including those that carry side chains to which are appended functional groups, such as fluorescent, fluorescent quencher, attachment, or metal complexing groups. Which organic molecule is chosen to implement a specific hydrogen bonding pattern determines, in large part, the utility of the non-standard hydrogen bonding pattern, in various applications to which it might be applied.

The structures disclosed by U.S. Pat. No. 6,140,496, as well as its predecessor patents, provide for an expanded molecular recognition system by providing more than four independently recognizable building blocks that can be incorporated into DNA and RNA.

Should the additional nucleobase pairs be placed into DNA and RNA, and if once so placed they have the desirable pairing properties, chemical stability, and other features known to those skilled in they art, they could be useful for a variety of purposes. For example, RNA molecules prepared by transcription, although it is known to be a catalyst under special circumstances [Cech, T. R.; Bass, B. L (1986). *Ann. Rev. Biochem.* 55, 599][Szostak, J. W. (1986) Nature 332, 83. Been, M. D.; Cech, T. R. (1988) *Science* 239, 1412], appear to have a much smaller catalytic potential than proteins because they lack building blocks bearing functional groups. Conversely, the limited functionality present on natural oligonucleotides constrains the chemist attempting to design catalytically active RNA molecules, in particular, RNA molecules that catalyze the template-directed polymerization of RNA.

Likewise, additional nucleobase pairs can be incorporated enzymatically at specific positions in an oligonucleotide molecule [Switzer, C. Y, Moroney, S. E., Benner, S. A. (1989) *J. Am. Chem. Soc.* 111, 8322]. If functionalized, such additional nucleobases should also allow the incorporation of functional groups into specific positions in a DNA or RNA sequence. A polymerase chain reaction has been demonstrated using a variant of an HIV reverse transcriptase to incorporate the pair between 2,4-diamino-5-(1'-beta-D-2'-deoxyribofuranosyl)-pyrimidine, implementing the pyDAD hydrogen bonding pattern, and 3,9-dihydro-9-(1'-beta-D-2'-deoxyribofuranosyl)-1H-purine-2,6-dione, implementing the puADA hydrogen bonding pattern [Sismour, A. M., Lutz, S., Park, J.-H., Lutz, M. J., Boyer, P. L., Hughes, S. H., Benner, S. A. (2004) PCR amplification of DNA containing non-standard base pairs by variants of reverse transcriptase from human immunodeficiency virus-1. *Nucl. Acids. Res.* 32, 728-735]. As standard nucleobases bearing functional groups at the 5-position of the uridine ring are accepted as substrates for most polymerases [Leary, J. L., Brigati, D. J., Ward, D. C. (1983) *Proc. Natl. Acad. Sci.* 80, 4045], non-standard nucleobases that are modified at the analogous positions are also accepted, provided that the polymerase accepts the parent non-standard nucleobase. New nucleobase pairs should also find use in studies of the structure of biologically important RNA and DNA molecules [Chen, T. R., Churchill, M. E. A. Tullius, T. D. Kallenbach, N. R., Seemann, N. C. (1988) *Biochem.* 27, 6032] and protein-nucleic acid interactions. They should also be useful in assembling nanostructures, including branched DNA useful for diagnostics, or for nanomachines. Further, non-standard nucleobases can be used to expand the genetic code, increasing the number of amino acids that can be incorporated translationally into proteins [Bain, J. D., Chamberlin, A. R., Switzer, C. Y., Benner, S. A. (1992) Ribosome-mediated incorporation of non-standard amino acids into a peptide through expansion of the genetic code. *Nature* 356, 537-539].

Some commercial applications have already been realized with the expanded genetic information systems disclosed by Benner in his patents. For example, the nucleobase pair between 2-amino-5-methyl]-(1'-beta-D-2'-deoxyribofuranosyl)-4(1H)-pyrimidinone, also known as 2'-deoxyisocytidine, disoC, or sometimes (less correctly) isoC and implementing the pyAAD hydrogen bonding pattern, and 6-amino-1,9-dihydro-9-(1'-beta-D-2'-deoxyribofuranosyl)-3H-purin-2-one, also known as 2'-deoxyisoguanosine, disoG, or sometimes (less correctly) isoG, and implementing the puDDA hydrogen bonding pattern, is incorporated into the branched DNA diagnostics tools marketed today by Bayer. Here, it provides molecular recognition on demand in aqueous solution, similar to nucleic acids but with a coding system that is orthogonal to the system in DNA and RNA. Thus, it prevents the assembly of the branched dendrimer in the assay from being inhibited by adventitious nucleic acid, and prevents adventitious nucleic acid from capturing signaling elements form the nanostructure in the absence of the target analyte nucleic acid, creating noise. Further, adding extra letters to the genetic alphabet speeds hybridization, presumably because it decreases the number of close mismatches where DNA dwells before finding its correct, fully matched partner. The branched DNA assay now has FDA-approval, and is widely used to provide personalized patient care in the clinic.

The Benner patents claimed a wide range of structures generally, but only a few specifically. The compounds specifically claimed, where those claims were supported by specific examples in the disclosure, were disclosed as the preferred implementations of the individual hydrogen bonding patterns, and are reproduced in FIG. 1 (taken from FIG. 2 of U.S. Pat. No. 6,140,496). Making reference to U.S. Pat. No. 6,140,496, the following implementations (where a systematic name is given for the 2'-deoxyribonucleoside; the corresponding ribonucleosides, 2'-O-methyl ribonucleosides, and various derivatives of these were also disclosed) were preferred as implementations for each of the hydrogen bonding patterns:

For the pyDAD hydrogen bonding pattern. The preferred embodiment disclosed in U.S. Pat. No. 6,140,496 supported the pyDAD hydrogen bonding pattern on the 2,4-diaminopyrimidine heterocycle. The specific deoxyribonucleoside was 2,4-diamino-5-(1'-beta-D-2'-deoxyribofuranosyl)-pyrimidine, also named (1R)-1,4-anhydro-2-deoxy-1-C-(2,4-diamino-5-pyrimidinyl)-D-erythropentitol.

For the puADA hydrogen bonding pattern. The preferred embodiment disclosed in U.S. Pat. No. 6,140,496 supported the pyDAD hydrogen bonding pattern on the xanthine heterocycle. The specific deoxyribonucleoside was 3,9-dihydro-9-(1'-beta-D-2'-deoxyribofuranosyl)-1H-purine-2,6-dione, also known as 9-(2'-deoxy-beta-D-ribosyl)-xanthine.

For the pyAAD hydrogen bonding pattern. The preferred embodiment disclosed in U.S. Pat. No. 6,140,496 supported the pyDAD hydrogen bonding pattern on the 5-methyl-isocytosine heterocycle. The specific deoxyribonucleoside was 2-amino-5-methyl-1-(1'-beta-D-2'-deoxyribofuranosyl)-4(1H)-pyrimidinone, For the puDDA hydrogen bonding pattern. The preferred embodiment disclosed in U.S. Pat. No. 6,140,496 supported the pyDAD hydrogen bonding pattern on the isoguanine heterocycle. The specific deoxyribonucleoside was 6-amino-1,9-dihydro-9-(1'-beta-D-2'-deoxyribofuranosyl)-3H-purin-2-one.

For the pyDDA hydrogen bonding pattern. The preferred embodiment disclosed in U.S. Pat. No. 6,140,496 supported the pyDAD hydrogen bonding pattern on the 6-amino-5-methyl-2(1H)-pyrazinone heterocycle. The specific deoxyribonucleoside was 6-amino-5-methyl-3-(1'-beta-D-2'-deoxyribofuranosyl)-2(1H)-pyrazinone.

For the puAAD hydrogen bonding pattern. The preferred embodiment disclosed in U.S. Pat. No. 6,140,496 supported the pyDAD hydrogen bonding pattern on the 5-aza-3,7-dideazaguanosine heterocycle. The specific deoxyribonucleoside was 2-amino-1,9-dihydro-5-aza-3,7-dideaza-9-(1'-beta-D-2'-deoxyribofuranosyl)-1H-purin-6-one, also known as 7-amino-9-(1'-beta-D-2'-deoxyribofuranosyl)-imidazo[1,2-c]pyrimidin-5(1H)-one, For the pyADD hydrogen bonding pattern. The preferred embodiment disclosed in U.S. Pat. No. 6,140,496 supported the pyDAD hydrogen bonding pattern on the 6-amino-3-methyl-2(1H)-pyrazinone heterocycle. The specific deoxyribonucleoside was 6-amino-3-methyl-5-(1'-beta-D-2'-deoxyribofuranosyl)-2(1H)-pyrazinone, For the puDAA hydrogen bonding pattern. The preferred embodiment disclosed in U.S. Pat. No. 6,140,496 supported the pyDAD hydrogen bonding pattern on the 4-amino-1,3,5-triazin-2(8H)-one heterocycle. The specific deoxyribonucleoside was 4-amino-8-(2-deoxy-beta-D-erythro-pentofuranosyl)-imidazo[1,2-a]-1,3,5-triazin-2(8H)-one, also known as, 4-amino-8-(1'-beta-D-2'-deoxyribofuranosyl)-imidazo[1,2-a]-1,3,5-triazin-2(8H)-one.

Despite the value of the compositions disclosed by U.S. Pat. No. 6,140,496, it is clear that the specific compositions used to implement the various non-standard hydrogen bonding patterns were not optimal, at least from the perspective of potential utility. Several problematic physical and chemical properties of the compositions that were claimed specifically were disclosed in the specification of U.S. Pat. No. 6,140,496.

For example, the nucleobases that were, in U.S. Pat. No. 6,140,496, specifically disclosed as implementations of the pyADD and pyDDA hydrogen bonding patterns undergo an epimerization reaction that interconverts the beta and alpha anomers [von Krosigk, U., Benner, S. A. (1995) pH-independent triple helix formation by an oligonucleotide containing a pyrazine donor-donor-acceptor base. *J. Am. Chem. Soc.* 117, 5361-5362] [Vogel, J. J., von Krosigk, U. Benner, S. A. (1993) Synthesis and tautomeric equilibrium of 6-amino-5-benzyl-3-methylpyrazin-2-one. An acceptor-donor-donor nucleoside base analog. *J. Org. Chem.* 58, 7542-7547]. This is illustrated in FIG. 2.

It was noted that this epimerization diminished the utility of these nucleobases. U.S. Pat. No. 6,140,496 and its predecessors proposed to solve the epimerization problem by replacing the furanose ring system (which includes an oxygen in a ring) with a carbocyclic cyclopentane derivative (which does not, and therefore cannot epimerize). The carbocyclic nucleoside analog is, however, difficult to synthesize, and has other disadvantages, and has never been incorporated into a commercial product.

An alternative tactic proposed to manage the epimerization problem has the pyrazine heterocycles that were the preferred implementations of the pyDDA and pyADD hydrogen bonding implementations (respectively) attached to a ribose derivative where a lower alkyl, most preferably methyl, group is attached to the 2'-oxygen. The 2'-O-alkyl group is large, and it was proposed that although the undesired epimerization reaction interconverting the beta and alpha anomers would still occur, steric factors would cause the beta (desired) form to predominate at equilibrium. Again, this would create problems if multiple non-standard nucleobases implementing this hydrogen bonding pattern were incorporated into an oligonucleotide analog.

The specification of U.S. Pat. No. 6,140,496 and its predecessors, as well as the literature, disclose difficulties with the use of 6-amino-1,9-dihydro-9-(1'-beta-D-2'-deoxyribofuranosyl)-3H-purin-2-one (isoguanosine, or isoG) as the implementation of the puDDA hydrogen bonding pattern. In its major keto form, isoguanosine implements the desired puDDA hydrogen bonding pattern. Isoguanosine has long been known to exist, to about 10% of the total in water, in a minor enolic tautomeric form. The enolic tautomer presents the puDAD hydrogen bonding pattern that is complementary to the thymidine and uridine nucleobases. That is, about 10% of isoguanine presents the puDAD hydrogen bonding pattern, not the desired puDDA pattern. This was noted in this specification to inconvenience efforts to use polymerases to copy DNA molecules containing isoguanine-containing nucleotide units. Indeed, some polymerases prefer to place thymidine (T) and/or uridine (U), rather than isocytidine (isoC), opposite isoguanosine in a template. The disutility of this was recently shown by Johnson et al. [Johnson, S. C., Sherrill, C. B., Marshall, D. J., Moser, M. J., Prudent, J. R. (2004) A third base pair for the polymerase chain reaction: inserting isoC and isoG. *Nucl. Acids Res.* 32, 1937-1941], who attempted to do a polymerase chain reaction amplification of a DNA molecule, requiring the repeated copying of the isoguanine-isocytosine nucleobase pair implementing the puDDA-pyAAD hydrogen bonding patterns. As expected from the known tautomeric behavior of isoguanine, the isoG-isoC pair was lost during the PCR reaction, presumably due to mismatching between T and the minor tautomer of isoguanosine.

Other features of the compounds that were specifically disclosed in U.S. Pat. No. 6,140,496 and its predecessors as the preferred implementations of the various hydrogen bonding schemes narrow the scope of their utility. For example, the heterocycle of 3,9-dihydro-9-(1'-beta-D-2'-deoxyribofuranosyl)-1H-purine-2,6-dione heterocycle (xanthine) proposed to implement the puADA hydrogen bonding pattern, is an acid, having a $pK_a$ between 5 and 6. Thus, at neutral pH and higher, where many polymerases operate and where many applications of oligonucleotide analog recognition are desired, xanthine is deprotonated. Deprotonation creates a negative charge, which destabilizes the duplex structure [Geyer, C. R., Battersby, T. R., Benner, S. A. (2003) Nucleobase pairing in expanded Watson-Crick like genetic information systems. The nucleobases. *Structure* 11, 1485-1498]. It is considered unlikely that multiple xanthines in an oligonucleotide analog would support rule-based molecular recognition effectively.

Likewise, the 2,4-diamino-5-(1'-beta-D-2'-deoxyribofuranosyl)-pyrimidine proposed to implement the pyDAD hydrogen bonding pattern carries a positive charge at pH 7.0, as it is a relatively good base. Further, the synthesis of the 2'-deoxyribonucleoside bearing this nucleobase is long and expensive.

Likewise, the specifically disclosed nucleoside analogs that implement the puAAD hydrogen bonding pattern on the 5-aza-3,7-dideazaguanosine heterocycle may be poor substrates for many DNA and RNA polymerases, especially those that make contact to an unshared pair of electrons in the minor groove [Steitz, T. in Burnett, R. M. and Vogel, H. J. (eds.) *Biological Organization: Macromolecular Interactions at High Resolution*; Academic Press: New York, 1987, pp. 45-55.]. This limits the utility of triphosphates of nucleoside analogs bearing this heterocycle as a substrate for a DNA polymerase, an RNA polymerase, and reverse transcriptases, as well as the utility of oligonucleotide analogs carrying this heterocycle as templates for these enzymes. This is also the case for derivatives which attach an alkyl group to the N-3 of the purine or purine analogs (in the analogous positions). In U.S. Pat. No. 6,140,496 and its predecessors, various N-3 methylated purines are disclosed as implementations of various hydrogen bonding patterns.

Likewise, the implementation of the pyAAD hydrogen bonding pattern using 5-alkylisocytidine derivatives proves to present difficulties. Deoxyribosides bearing the 2-amino-5-methyl-1-(1'-beta-D-2'-deoxyribofuranosyl)-4(1H)-pyrimidinone (also know as 5-methylisocytosine) is sensitive to depyrimidinylation, the cleavage of the 1-1' nitrogen-carbon bond to separate the heterocycle from the sugar, under acidic conditions. Considerable effort was devoted to developing the delicate synthetic procedures needed to prepare oligonucleotide analogs that contain multiple 2-deoxyisocytidines, increasing the expense of the synthesis. The acid sensitivity extends to the oligonucleotides in solution, diminishing their utility.

One purpose of the instant disclosure is to provide nucleobase analogs (where "nucleobase" refers to the heterocycle, or aglycone) that implement non-standard hydrogen bonding patterns, said analogs having properties improved over those analogs of the prior art that implement their respective hydrogen bonding patterns. In particular, the compositions of the instant invention mitigate or avoid entirely the limitations listed above of the compositions that were disclosed in U.S. Pat. No. 6,140,496.

One of ordinary skill in the art would find these improved properties unexpected, even in the light of the disclosures in patents and other literature of the prior art, and that find unexpected the greater utility that these nucleobase analogs have compared to the compositions disclosed in the prior art to implement this hydrogen bonding pattern.

Another purpose of the instant disclosure is to provide nucleoside analogs (where "nucleoside analog" is an analog of the heterocycle together with the sugar or sugar analog) that carry the nonstandard nucleobase analog, where the sugar is 2'-deoxyribose or ribose, as well as analogs where the sugar is modified, as in 2'-O-methyl, 2'-O-allyl, 2'-deoxy-2'-fluoro, and 2',3'-dideoxynucleoside derivatives, as well as nucleoside analogs based on other sugar backbones, such as threose, locked nucleic acid derivatives, bicyclo sugars, or hexose, glycerol and glycol sugars [Zhang, L., Peritz, A., Meggers, E. (2005) A simple glycol nucleic acid. *J. Am. Chem. Soc.* 127, 4174-4175].

Another purpose of the instant invention is to provide oligonucleotide analogs that incorporate one or more of the nonstandard nucleoside analogs. These include nucleic acid analogs that incorporate the sugars and sugar analogs mentioned in the previous paragraph, as well as oligonucleotide analogs based on non-ionic backbones, such as "peptide nucleic acids".

Another purpose of the instant invention is to provide nucleoside analogs in protected form that are suitable as precursors for the non-enzymatic synthesis of the non-standard oligonucleotide analogs.

Another purpose of the instant invention is to provide various phosphorylated derivatives of the stated nucleoside analogs, including triphosphates, which have utility in various enzymatic processes for the synthesis of the oligonucleotide analogs stated above.

Another purpose of the instant invention is to provide derivatives of the nucleoside analogs stated above that are degradation products of the oligonucleotide analogs stated above, and therefore help (for example) analyze these.

Another purpose of the instant invention is to provide 2',3'-dideoxy analogs of the nucleoside analogs mentioned above, 3'-$ONH_2$ derivatives, and other analogs and derivatives useful for the purpose of sequencing the oligonucleotide analogs mentioned above.

Another purpose of the instant invention is to provide compositions of matter wherein the oligonucleotide analogs mentioned above are attached to a solid phase, including a bead or microsphere, a two dimensional surface as part of a two dimensional array, and in a one dimensional array.

Another purpose of the instant invention is to provide processes for synthesizing said oligonucleotide analogs, both through template-directed polymerization and non-template-directed polymerization.

Another purpose of the instant invention is to provide processes for utilizing the compositions of matter described above. These include a variety of architectures that exploit a process that binds the stated oligonucleotide analogs to complementary oligonucleotide analogs containing one or more nucleobases that implements the complementary non-standard hydrogen bonding pattern, following an expanded set of Watson-Crick rules involving 6, 8, 10, and 12 letter DNA/RNA alphabets. These architectures include (without limitation) the stated oligonucleotide analogs as parts of compositions of matter that are beacons, nanostructures, dendrimers, and branched DNA molecules, and attached to solid supports such as beads, one dimensional arrays, two dimensional arrays, polonies, standard gels, and thermoresponsive gels, or in solution.

Another purpose of the instant invention is to provide oligonucleotide analogs as mentioned above for use in various architectures for detecting and sequencing oligonucleotides and oligonucleotide analogs, including within molecular beacons, in one and two dimensional arrays, on beads, in dendrimers that include both branched DNA and dendrimeric structures incorporating non-nucleosidic branching units, in assays involving cleavage reactions, in taggants and taggant detection schemes, and in nanostructures.

Another purpose of the instant invention is to provide the processes for utilization of the above described oligonucleotide analogs in the architectures above.

Another purpose of the instant invention is to provide functionalized derivatives of the nucleoside analogs mentioned above, carrying appendages that are fluorescent or that quench fluorescence, that assist in immobilization, that provide metal coordination sites, and that catalyze reactions, inter alia, when incorporated into the oligonucleotide analogs mentioned above, and into the processes mentioned above.

Another purpose of the instant invention is to provide processes for the repeated copying of the stated oligonucleotide analogs using template-directed polymerization, and copying of the copies in a polymerase chain reaction, having utility in oligonucleotide analog amplification, detection, and in vitro evolution to generate aptamers and oligonucleotide catalysts.

Another purpose of the instant invention is to provide non-standard nucleobases that are easily incorporated by DNA polymerases, RNA polymerases, and reverse transcriptases into the products of template-driven oligonucleotide synthesis. Various analyses of the interaction between polymerases and their substrates suggest that the polymerase seeks two unshared pairs of electrons in the minor groove, at position 3 of the purine (or analog) and at position 2 of the pyrimidine (or analog) [Steitz, T. in Burnett, R. M. and Vogel, H. J. (eds.) *Biological Organization: Macromolecular Interactions at High Resolution*; Academic Press: New York, 1987, pp. 45-55]. In addition, the base pairs that form three hydrogen bonds are expected to contribute more to duplex stability than pairs joined by just two hydrogen bonds.

These conditions are fulfilled for the compounds disclosed herein for implementing the pyDDA:puAAD hydrogen bonding pattern.

Schematic showing the synthesis of nucleobases of the instant invention as their 2'-deoxyribosides, phosphoramidites, and triphosphates.

Figure 10:
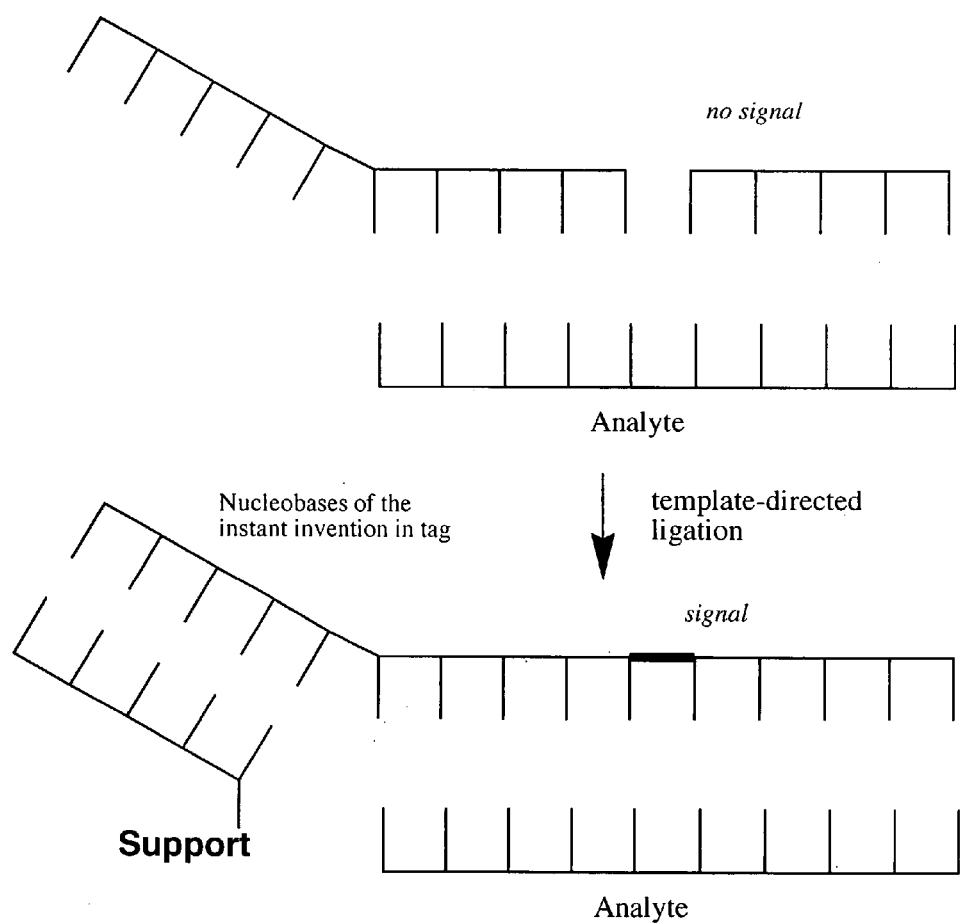

FIG. 10. An architecture using the oligonucleotide analogs of the instant invention in tags in a detection scheme. The architecture illustrates the process of binding two oligonucleotide analogs of the instant invention, and the use of solid supports.

Figure 11:
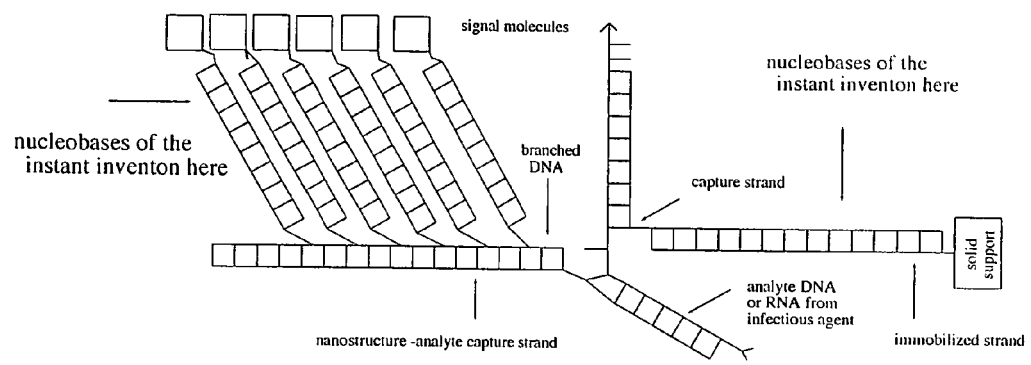

FIG. 11. An architecture using the oligonucleotide analogs of the instant invention in tags in a dendrimeric structure.

Figure 12:
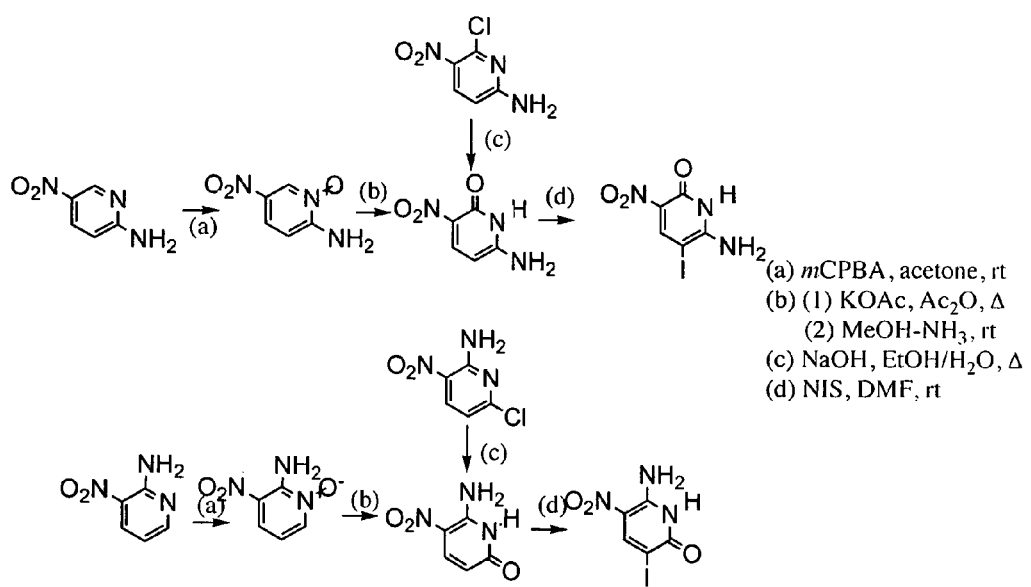

FIG. 12. Synthesis of precursors for the pyADD implementation, showing analogy with the synthesis of precursors for the pyDDA implementation.

Figure 13:
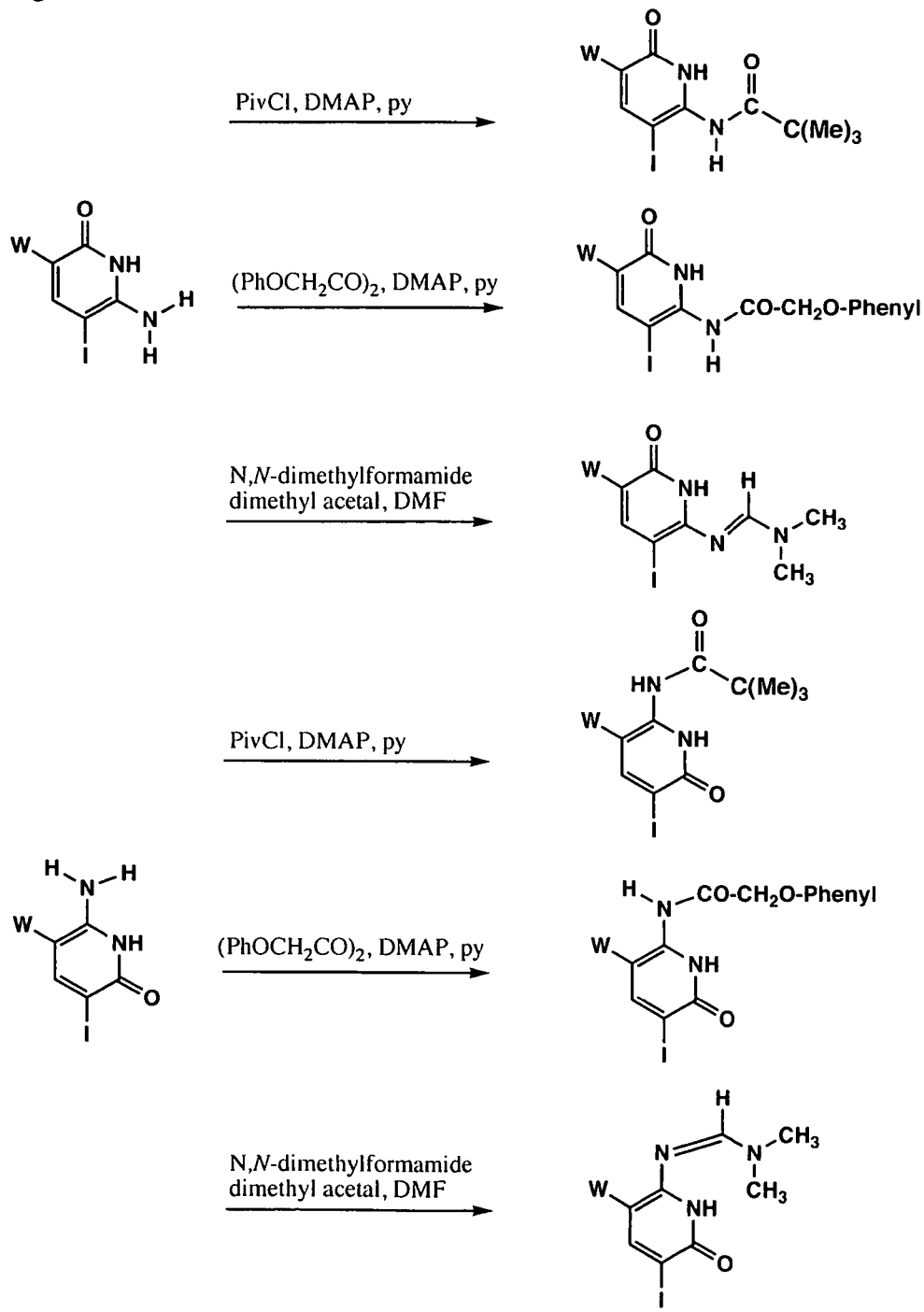

FIG. 13. Synthesis of protected precursors for the pyADD implementation, and the protected precursors for the pyDDA implementation.

Figure 14:
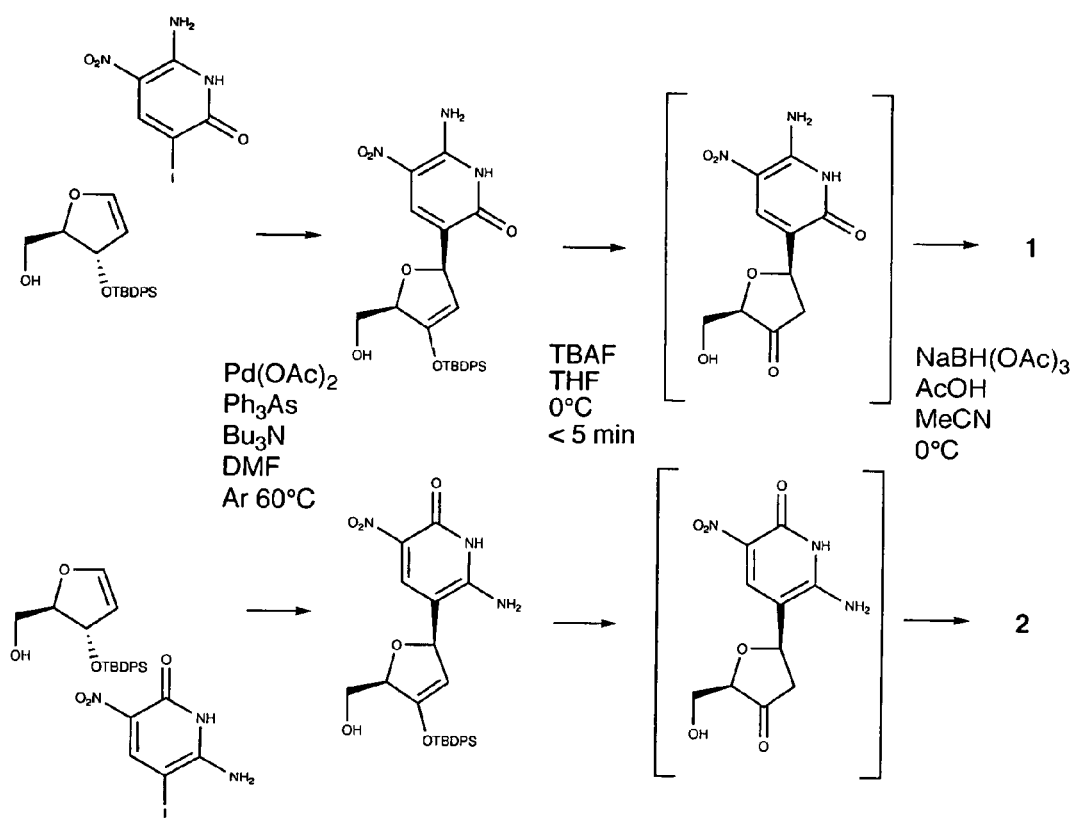

FIG. 14. Coupling of the glycal to the unprotected precursors for the pyADD implementation, and the unprotected precursors for the pyDDA implementation.

Figure 15:
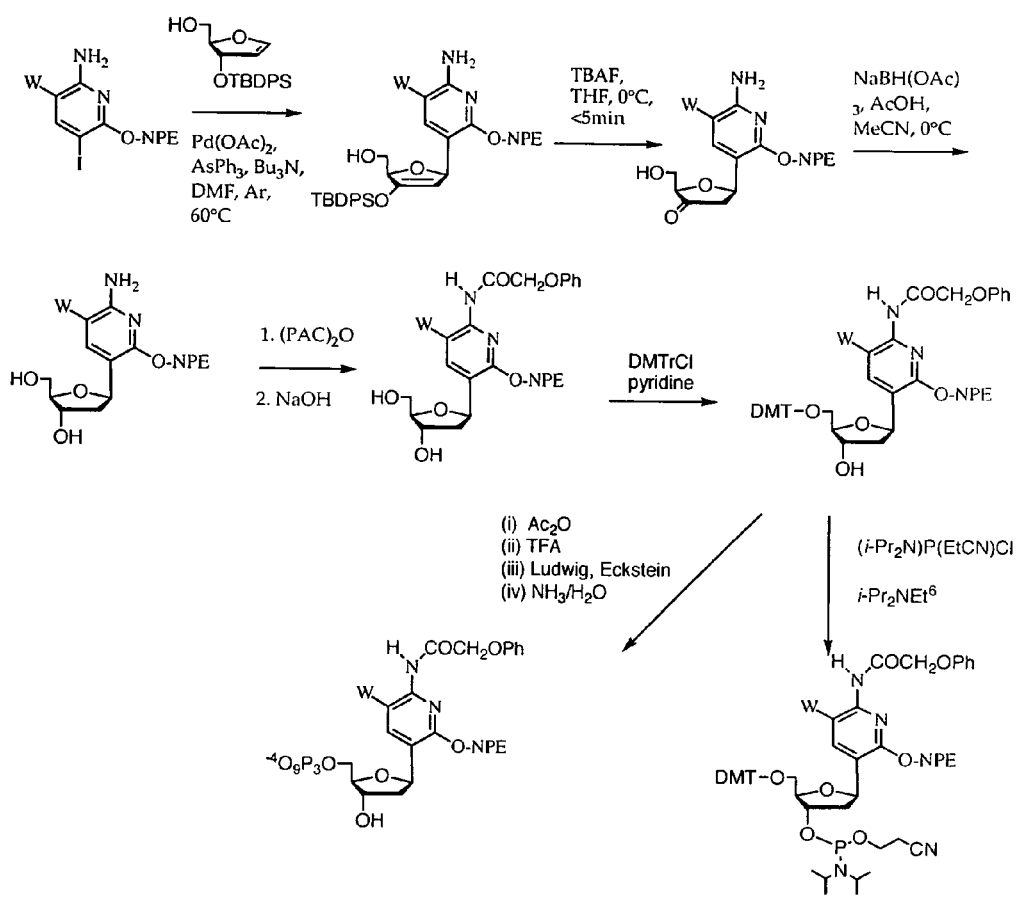

FIG. 15. Coupling of the protected precursors for the pyADD implementation, and the protected precursors for the pyDDA implementation.

Figure 16:
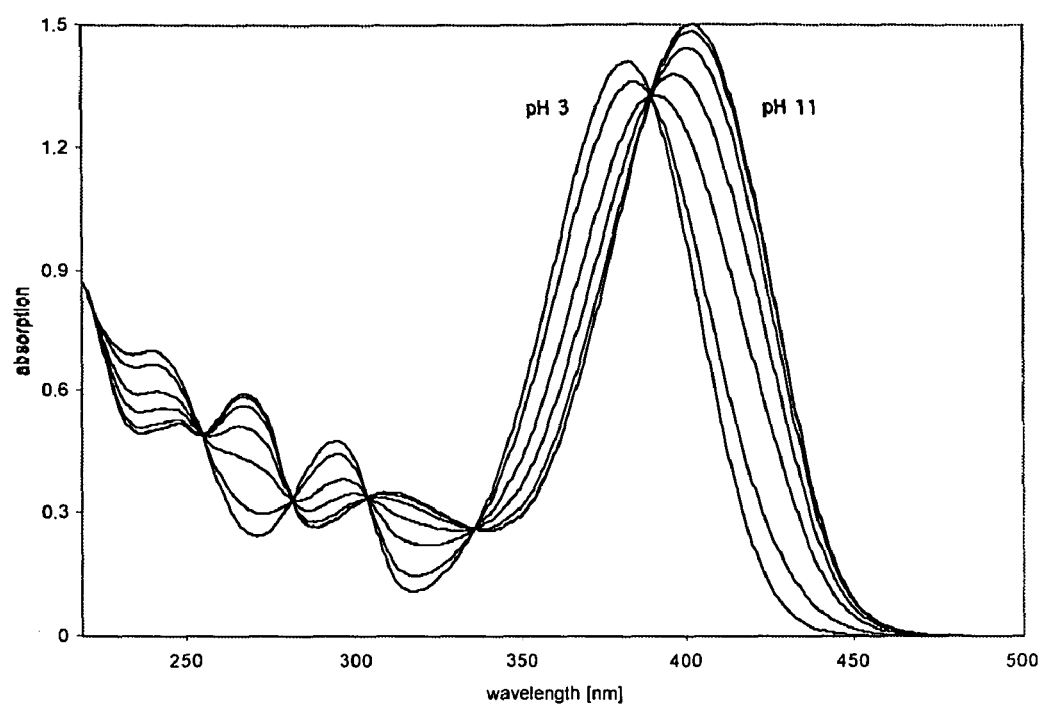

FIG. 16. Titration of nucleoside analog 4 (UV absorbance versus wavelength) showing a $pK_a$ of 7.8±0.1.

Figure 17:
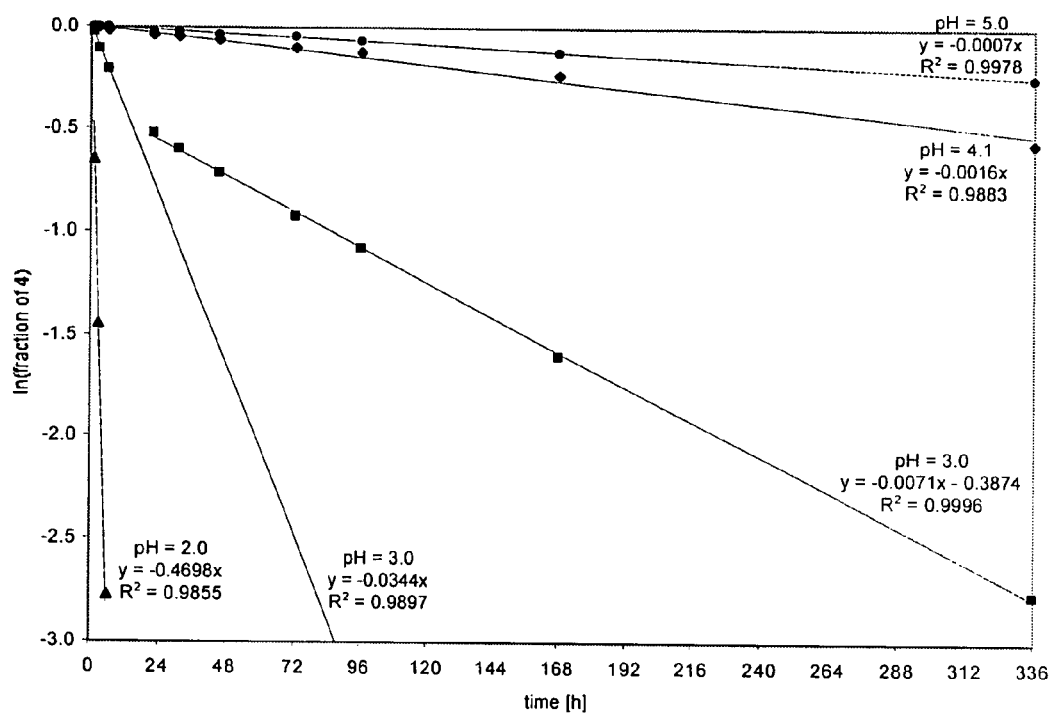

FIG. 17. Acid-catalyzed epimerization of nucleoside 4. Natural log of the fraction of 4 remaining after time t versus t at pH 2.0, 3.0, 4.1 and 5.0 (37° C., aqueous).

Figure 18:
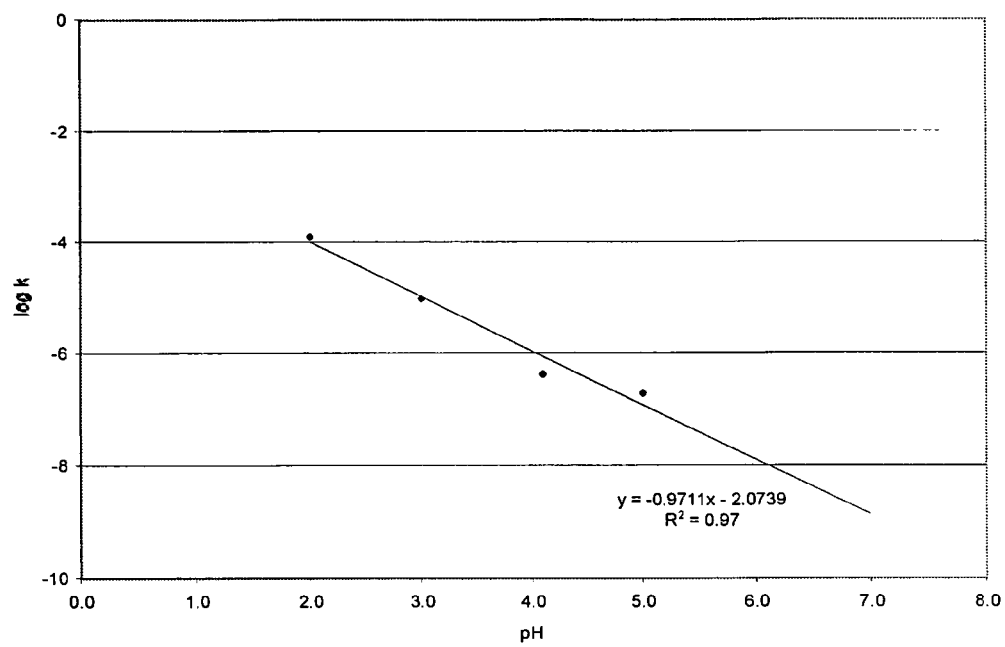

FIG. 18. Replot of log $k_{apparent}$ versus pH, showing a first order dependence of the epimerization reaction with hydrogen activity.

DESCRIPTION OF INVENTION

The pyDDA, pyADD, and pyDAD Analogs on Sugars

In the prior art, it was noted that the pyDDA hydrogen bonding pattern can be achieved in an uncharged species only with a C-glycoside, where the heterocycle is coupled to the sugar moiety by a C—C bond. The C-glycoside structure is different from the "N-glycosidic" structure found in the standard nucleosides, where the heterocycle is coupled to the sugar moiety by a C—N bond.

A special feature of C-nucleosides is their susceptibility to epimerization if an electron donating substituent is present in a suitable position on the heterocycle. This phenomenon was described for pseudouridine several decades ago [Cohn, W. E. (1960) *J. Biol. Chem.* 235, 1488.] and for other C-nucleosides since [Chambers, R. W.; Kurkov, V.; Shapiro, R. (1963) *Biochemistry.* 2, 1192.].

In the Benner laboratory, it was shown that C-nucleosides displaying the pyDDA hydrogen bonding pattern, and with 5'- and 3'-hydroxyls epimerize, usually in either acidic or basic medium, to a mixture of four isomers with the pyranose forms being the most abundant [Voegel, J. J.; Benner, S. A. (1994) *J. Am. Chem. Soc.* 116, 6929.] [von Krosigk, U.; Benner, S. A. (1995) *J. Am. Chem. Soc.* 117, 5361.][Voegel, J. J.; Benner, S. A. (1996) *Helv. Chim. Acta* 79, 1863]. With the hydroxyls protected or substituted, the epimerization limits itself to the α/β-forms of the furanoses. This epimerization is problematic, especially during the acidic deprotection step of the 5'-position during solid phase oligonucleotide synthesis. Further, the C-nucleoside, both in solution and when incorporated into an oligonucleotide, will also epimerize upon standing at pH 7 for a prolonged period of time.

The epimerization of the nucleoside analogs, which are based on pyrazine heterocyclic systems, reported in the prior art to implement the pyDDA and pyADD hydrogen bonding patterns, while useful in some contexts (for example, in facilitating the linear amplification of oligonucleotides containing these implementations of the pyDDA and pyADD hydrogen bonding patterns), causes these nucleobase analogs to have severely diminished utility. It may also cause the loss of utility of the pyDAD implementation disclosed in the prior art. It also causes the nucleobase pair with the corresponding purine nucleobase analogs implementing the complementary puAAD and puDAA hydrogen bonding patterns to lack much of their potential utility.

The Inventor set out to design compositions of matter that ameliorate the epimerization properties. While not wishing to be bound by theory, the Inventor recognized that the epimerization is specific acid catalyzed. He therefore considered that the rate of epimerization could be reduced by adjusting the electronic distribution in the heterocyclic ring. He reasoned that an electron withdrawing group on the 5-position (where the numbering system used is defined to highlight the analogy to pyrimidine nucleosides, even in cases where the position of heteroatoms in the heterocyclic ring would cause the IUPAC numbering to be different) would draw the electrons away, so that they do not push the furanose ring system open, the first step in the epimerization process. A substituents at this position would not interfere with Watson-Crick pairing, nor with acceptance by polymerases and reverse transcriptases. Further, the electron withdrawing group would make the heterocycle less basic and less susceptible to oxidation than the pyridine heterocycle, making the second nitrogen in the pyrazine ring unnecessary for these purposes.

A survey of the prior art found no literature that taught that the addition of an electron withdrawing group to a pyridine heterocycle would support the pyDDA and pyADD hydrogen bonding patterns of an artificially expanded genetic information system.

In principle, any of a number of electron withdrawing groups are conceivable for this purpose. Three of these are presently preferred, the cyano group, the nitro group, and an uncharged derivative of a carboxylic acid (an ester or amide). Also preferred are the cyano, carboxyl ester, or a carboxamido unit via an unsaturated linker (double or triple bond). The ester and amino groups have special value if appending a functional group is desired (e.g., a fluorescent group, a fluorescence quenching group, a metal liganding group, a catalytically active group, a group for binding to another species, or a group for capturing the oligonucleotide analog to a solid support) be desired at this site.

None of these structures are covered by claims in the prior patent literature, or structures in the literature, other than that published by the Inventor less than a year prior to the provisional patent whose priority date the instant application claims. Thus, the 4-amino-pyridine-2-one, 2-amino-pyridine-4-one, and 2,4-diaminopyridine heterocycles fall within the claim structures, and while these structures included the attachment of a substituents at position 5, this substituents was designated to be an alkyl substituent. Neither the cyano group, the nitro group, nor an uncharged derivative of a carboxylic acid (an ester or amide) were included within the structures claimed, nor were the cyano, carboxyl ester, or a carboxamido unit via an unsaturated linker (double or triple bond) included. Nor were the structures nor their utility taught in the prior patents.

It is taught that the nucleobase analogs of the instant invention can be used as a component of an oligonucleotide to bind to a complementary oligonucleotide, where a nucleobase analog in the complementary oligonucleotide is complementary, according to the expanded Watson-Crick rules to the nucleobase analog of the instant invention. Further, it is taught that the nucleobase analogs of the instant invention can be used in oligonucleotide analogs containing a full range of other nucleobases and nucleobase analogs, either those in the literature or improvements as may emerge from time to time, implementing (in the extreme case) a full 12 letter genetic alphabet.

The synthesis of the nucleoside analogs of the instant invention uses as a key step the Heck coupling of a iodinated heterocycle with the non-standard hydrogen bonding pattern to 3-tertbutyldiphenylsilyloxy-2-hydroxymethyl-2,3-dihydrofuran, which is known in the literature, and referred to here as simply the "glycal" [Ireland, R. E., Thaisrivongs, S., Vanier, N., Wilcox, C. S. (1980) *J. Org. Chem.* 45, 48][Larsen, E., Jorgensen, P. T., Sofan, M. A, Pedersen, E. B. (1994) *Synthesis*, 1037-[[Walker II, J. A., Chen, J. J., Wise, D. S., Townsend, L. B. (1996) *J. Org. Chem.* 61, 2219][Cameron, M. A.; Cush, S. B.; Hammer, R. P. (1997) *J. Org. Chem.* 62, 9065.][Hutter, D., Benner, S. A. (2003) Expanding the genetic alphabet. Non-epimerizing nucleoside with the pyDDA hydrogen bonding pattern. *J. Org. Chem.* 68, 9839-9842].

The iodinated heterocycles to prepare the pyDDA and pyADD analogs of the instant invention are themselves prepared from the appropriate precursor pyridinones. Two routes, both well exemplified in the literature, are available to prepare these precursor pyridinones. In one route, the amino-3-pyridine bearing the electron withdrawing group is via a Katada rearrangement of the corresponding N-oxide, which is obtained by oxidizing the pyridine with mCPBA [Deady, L. W. (1977) *Synth. Commun.* 509.][Daeniker, H. U., Druey, J. (1958) *Helv. Chim. Acta* 41, 2148.][Taylor, E. C., Driscoll, J. S. (1960) *J. Org. Chem.* 25, 1716][Markgraf, J. H., Brown, Jr., H. B., Mohr, S. C, Peterson, R. G. (1962) *J. Am. Chem. Soc.* 85, 958.][McKillop, A., Bhagrath, M. K. (1985) *Heterocycles* 23, 1697.][Sato, N., Miwa, N., Suzuki, H., Sakakibara, T. (1994) *J. Heterocyclic Chem.* 31, 1229.].

The second route, which works in higher yield for several of the heterocycles [Hutter, D., Benner, S. A. (2003) Expanding the genetic alphabet. Non-epimerizing nucleoside with the pyDDA hydrogen bonding pattern. *J. Org. Chem.* 68, 9839-9842], starts with a 2,6-dichloropyridine derivative bearing the electron withdrawing group at the 3-position (e.g., the commercial 2,6-dichloro-3-nitropyridine). Aminolysis gives the corresponding aminochloropyridine derivative [Radl, S., Hradil, P. (1991) *Coll. Czech. Chem. Commun.* 56, 2420.]. This is hydrolyzed to the aminopyridone derivative with aqueous sodium hydroxide.

The appropriate aminopyridone bearing an electron group is then converted to the iodo heterocycle for coupling to the glycal. This is accomplished via iodination at the 5-position with N-iodosuccinimide (NIS) in DMF.

The Heck coupling is done following literature procedures, using palladium acetate with triphenylarsine as the catalyst system, and anhydrous dimethylformamide (DMF) as the solvent. The coupling to the glycal and subsequent deprotection and reduction have been reported previously by several groups [Farr, R. N. Outten, R. A. Cheng, J. C.-Y. Daves, Jr., G. D. (1990) *Organometallics* 9, 3151.][Zhang, H.-C. Daves, Jr., G. D. (1992) *J. Org. Chem.* 57, 4690][Zhang, H.-C. Daves, Jr., G. D. (1993) *Organometallics* 12, 1499.][Hsieh, H.-P. McLaughlin, L. W. (1995) *J. Org. Chem.*, 60, 5356][Chen, D. L. McLaughlin, L. W. (2000) *J. Org. Chem.*, 65, 7468.][Searls, T. Chen, D. L. Lan, T. McLaughlin, L. W. (2000) *Biochemistry*, 39, 4375.][Lan, T.; McLaughlin, L. W. (2001) *Bioorg. Chem.* 29, 1981-[Coleman, R. S., Madaras, M. L. (1998) *J. Org. Chem.* 63, 5700]. Triethylamine is often used instead of tributylamine as the base, since it is easier to remove during purification. Ca.1.2 equivalents of glycal are used. After several days at 60° C., the β-nucleoside is obtained. The bulky TBDPS group at the 3'-position is assumed to direct addition of the heterocycle to the β-face Rapid removal of the 5'-protective group with TBAF at 0° C. gives the corresponding ketones without any significant epimerization. The crude ketone must be reduced immediately with NaBH(OAc)$_3$ to give the final nucleoside. The free 5'-hydroxyl is presume to lead to stereospecific reduction of the ketone by complexation with the borohydride reagent. The products are purified by reverse phase HPLC.

To establish that the nitropyridine implementation of the pyDDA and pyAAD hydrogen bonding patterns on a 2'-deoxyriboside analog do not epimerize, and therefore lacks the disutility of the implementations known in the prior art, a variety of physical studies were done on the compound correctly known as 6-amino-5-nitro-3-(1'-beta-D-2'-deoxyribofuranosyl)-2(1H)-pyridone.

Thus, the pK$_a$ of this pyridone was measured by titrating an aqueous solution of the nucleoside with dilute aqueous solutions of HCl and NaOH and recording a UV spectrum at different pH values. The UV spectra displayed several isosbestic points. Analysis of the curves gave a pK$_a$ value of 7.8±0.1, which is ca. 2 pK$_a$ units lower than those for the natural nucleosides. Nevertheless, the nucleoside is largely (>80%) protonated at physiological pH, and still more protonated when embedded into a polyanionic DNA or RNA chain. Such embedding generally elevates the pK$_a$ of the nucleotide by about 0.5 units.

To measure the rate of epimerization of the nucleoside at neutral pH, a sample was dissolved in D$_2$O and stored at room temperature. The $^1$H NMR was measured after several time intervals. The spectrum did not change after one week. In particular, the NMR signal arising from H-6 of the heterocycle remained unchanged. This suggested that the compound was stable towards epimerization at neutral pH, and allowed for analysis by HPLC to measure the epimerization rate at other pH values.

For those measurements, the pH of an aqueous solution of the nucleoside analog (ca. 5 mM) was adjusted with dilute aqueous NaOH or HCl to the desired values. These solutions were incubated at constant temperature. After given time intervals, aliquots were removed, neutralized and subjected to analysis by reverse phase HPLC.

At high pH (pH 11.0), no epimerization was detected at 23° C. even after 14 days. The HPLC trace showed still only a single peak, corresponding to the starting material. This is consistent with the specific acid catalysis mechanism proposed by Voegel & Benner [Voegel, J. J., Benner, S. A. (1996) Helv. Chinn. Acta 79, 1863] for the C-glycoside in the art that implements the pyDDA hydrogen bonding pattern, and suggests that C-glycosides employ a specific acid mechanism for epimerization somewhat more generally.

Figure 4:
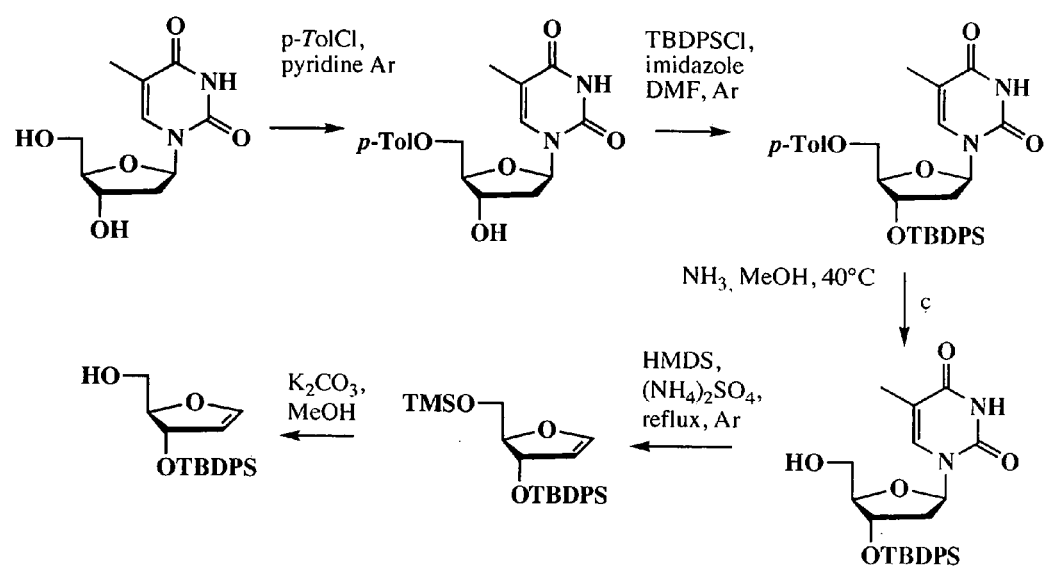
FIG. 4. Schematic showing the synthesis of the glycal that is a precursor of the nucleoside analogs of the instant invention.

At low pH (2.0 to 5.0) and 37° C. (used to speed the reaction), HPLC analysis showed the formation of four different compounds, as expected from an epimerization process. The initial rate of epimerization displays pseudo first order rate constants $k_{pH2} \approx 10^{-4}$ s$^{-1}$ at pH 2.0 and $k_{pH5} \approx 2 \times 10^{-7}$ s$^{-1}$ at pH 5.0 (FIG. 4). A replot of logk versus pH is linear within experimental error with a slope of −0.971, suggesting that the rate process is first order in hydrogen ion concentration consistent with specific acid catalysis.

As pH's below 5 are rarely used with standard oligonucleotides (the cytidine and adenine nucleobases protonate, and the adenine and guanine nucleobases depurinate at low pH), this does not diminish the utility of the analogs of the instant invention.

EXAMPLES

Example 1

Preparation of the Nucleoside Analogs of the Instant Invention

Preparation of the glycal. See [Hutter, D., Benner, S. A. (2003) Expanding the genetic alphabet. Non-epimerizing nucleoside with the pyDDA hydrogen bonding pattern. J. Org. Chem. 68, 9839-9842].

Figure 3:
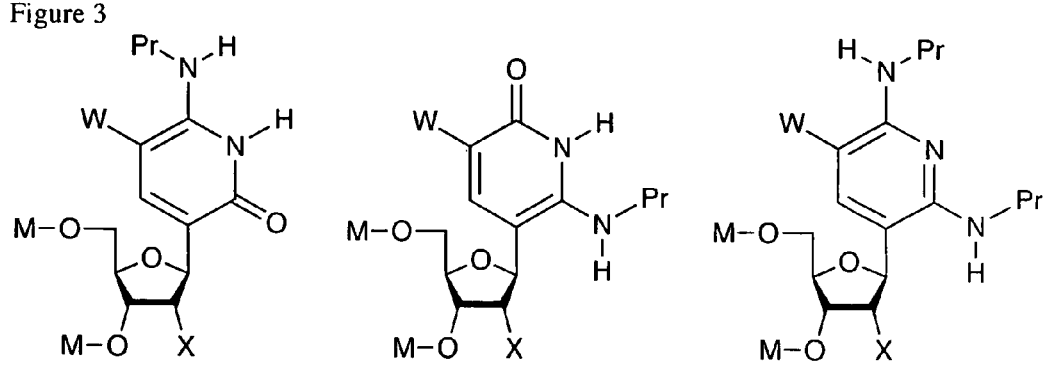
FIG. 3. The nucleobases of the instant invention on a variety of sugar scaffolds.

5'-p-Toluoylthymidine (FIG. 3)

p-Toluoyl chloride (6.78 mL, 51.25 mmol) was added dropwise (to keep the temperature of the mixture below 5° C.) to a cooled (ice/water bath) stirred suspension of thymidine (12.112 g, 50 mmol) in anhydrous pyridine (50 mL) under an argon atmosphere. After complete addition, the bath was removed and the mixture was allowed to warm to room temperature. After 16.5 h, thin layer chromatography (using EtOAc as eluant) showed that no starting material was remaining. The mixture was poured into ice (50 g), and after the ice melted, a white precipitate was collected by filtration. The aqueous filtrate was extracted with CH$_2$Cl$_2$ (3×50 mL) and the combined organic extracts were washed with 1M HCl (3×50 mL), saturated aqueous NaHCO$_3$ (3×50 mL) and water (3×50 mL). The CH$_2$Cl$_2$ solution was dried (MgSO$_4$), filtered and the filtrate concentrated under reduced pressure to give a pale yellow foam (3.00 g). The solid material was combined, and recrystallized in ca. 2 g batches from CH$_2$Cl$_2$ (300 mL). After each filtration, the volume of the filtrate was reduced to 100 mL and cooled. A white solid crystallizing from solution was collected by filtration. This filtrate was used as the solvent for the next crystallization. This was done multiple times. The insoluble solids removed after each crystallization were combined and recrystallized as above.

3'-TBDPS-5'-Toluoylthymidine

TBDPSCl (0.26 mL, 1.1 mmol) was added to a stirred solution of the product from above (0.360 g, 1.0 mmol) and imidazole (0.218 g, 3.2 mmol) in DMF (5 mL) under an atmosphere of Ar. The reaction was stirred at room temperature for 48 h. If TLC (2; 1 EtOAc:hexanes) showed that unreacted starting material remained, additional TBDPSCl (0.26 mL, 1.1 mmol) was added, and stirring was continued an additional 24 h. Concentration under vacuum without heat gave an oil, which was taken up in CH$_2$Cl$_2$ (10 mL) and washed with HCl 1M aqueous, (3×10 mL), sat NaHCO$_3$ (3×10 mL), water (3×10 mL), dried (MgSO$_4$), filtered and the filtrate concentrated under reduced pressure to give crude 3'-TBDPS-5'-toluoylthymidine as a pale yellow gum.

3'-TBDPS-thymidine

A solution of methanolic ammonia (saturated) was added to crude product from above (0.923 g). The reaction vessel was sealed with a septum and the reaction mixture was stirred at 40° C. for 2 days. The solvent was removed under reduced pressure to give crude 3'-TBDPS-thymidine as a pale yellow oil.

3-tertButyldiphenylsilyloxy-2-hydroxymethyl-2,3-dihydrofuran (the "glycal"

HMDS (5 mL) was added to crude the product from above (0.931 g) and powdered ammonium sulfate (0.025 g, 0.19 mmol) an atmosphere of argon. The reaction mixture was stirred and heated at reflux for 3 h. The reaction mixture was then removed from the heat. After it had cooled to room temperature, the solvent was removed under reduced pressure (high vacuum pump) without the use of a heat source. The resulting gum was taken up in cyclohexane (10 mL), washed with sat. NaHCO$_3$ solution (3×10 mL), dried (MgSO$_4$), filtered, and the filtrate concentrated under reduced pressure to give crude glycal 3-protected with TBDPS and 5-protected with TMS as a yellow oil. Purification by flash chromatography (1:5 EtOAc:hexanes) to give product as a colorless oil.

Example 2

Preparation of the pyDDA Heterocycle Via the N-Oxide

2-Amino-3-nitropyridine 1-oxide

To a solution of 2-amino-3-nitropyridine (5.0 g; 36 mmol) in acetone (250 mL) was added a solution of m-chloroperbenzoic acid (7.5 g; 100 mmol) in acetone (50 mL). The shiny orange solution was stirred at room temperature for 3 days. The resulting precipitate was dissolved again under heating and the solution poured onto a silica gel column. Column chromatography using acetone as eluant gave the title compound as an orange solid.

6-Amino-5-nitro-1H-pyridin-2-one from the N-oxide

A suspension of 2-amino-3-nitropyridine 1-oxide (506 mg; 3.3 mmol) and KOAc (330 mg; 3.3 mmol) in acetic anhydride (6 mL) was stirred at room temperature for 30 min and then heated under reflux in a preheated oil-bath (150° C.) for another 15 min. The dark brown solution was cooled to room temperature and the solvent removed under high vacuum. The residue was resuspended in ethanol (20 mL) and the solvent removed under high vacuum. The residue was extracted with refluxing dichloromethane (30 mL) for 3 days. A large amount of dark, fine solid remained, which was insoluble in water, acetone or DMSO. The dichloromethane solution was dried and the residue redissolved in methanolic ammonia (10 mL) and stirred at room temperature for 20 h. The volatiles were then removed to yield the pyridone as a slightly brownish powder. Treating the insoluble solids from the extraction with methanolic ammonia for several days did not yield any significant further amount of product. The analytical data were identical with those from method b) below.

Example 3

Preparation of the pyDDA Heterocycle Via the Dichloropyridine 2-amino-6-dichloro-3-nitropyridine 2,6-Dichloro-3-nitropyridine was suspended in MeOH, and the mixture was treated with ammonia at room temperature for 12 hours to yield 2-amino-3-nitro-6-chloropyridine. This was then treated with an ethanolic:aqueous solution of sodium hydroxide (10 M) at reflux to give 2-amino-3-nitro-6-(1H)-pyridinone. This was then treated with N-iodosuccinimide (1.05 equivalents) in dimethylformamide at room temperature to yield 2-amino-3-nitro-5-iodo-6-(1H)-pyridinone.

To a suspension of 2-amino-6-chloro-3-nitropyridine (4.38 g; 20 mmol) in refluxing ethanol (80 mL) and water (30 mL) was added an NaOH solution (aqueous 10 M, 16 mL). The resulting solution was heated under reflux for 5 min and then cooled on ice. Acidification with aqueous HCl (conc) generated a large amount of yellow precipitate. Filtration and drying over P$_2$O$_5$ gave the pyridone as a fine yellow powder.

Example 4

Preparation of the pyDDA Iodide

6-Amino-3-iodo-5-nitro-1H-pyridin-2-one

The pyridinone from above (2.17 g; 14 mmol) was rendered anhydrous by coevaporation with DMF under high vacuum and then resuspended in DMF (50 mL). N-Iodosuccinimide (4.73 g; 21 mmol) was added and the resulting solution was stirred at room temperature in the dark. After 4 days the solution was slowly added to vigorously stirred water (2 L) and the resulting suspension stirred overnight. Filtration and drying over P$_2$O$_5$ gave the product as a yellow solid.

Example 5

Protection of the Heterocycle

Preparation of 2-(4-nitrophenyl)-ethyl iodide

A solution of 2-(4-nitrophenyl)ethyl bromide (1.5 g, 6.52 mmol) and sodium iodide (2.0 g, 13.0 mmol) in acetone (28 mL) was stirred at 50° C. for 24 h under an atmosphere of Ar. After being cooled, the solids were removed from the mixture by filtration and the filtrate was concentrated under reduced pressure by rotary evaporation. The residue was dissolved in EtOAc (150 mL), washed with aqueous Na$_2$S$_2$O$_3$ solution (6%, 3×30 mL), then brine (3×25 mL). The organic portions were dried over Na$_2$SO$_4$, filtered, concentrated. The product was isolated as a white solid (1.8 g, 99%) by chromatography on a short column of silica gel using hexane/EtOAc (8:1) as the eluant.

NPE protection of the 5'-TBDMS-3'-TBDPS-protected nucleoside analog

2-Amino-3-nitro-5-iodopyridine (456 mg, 1.62 mmol) and silver carbonate (670 mg, 2.4 mmol) were heated at reflux in anhydrous benzene (30 mL) for 45 minutes. The mixture was cooled to 60° C., and 2-(4-nitrophenyl)-ethyl iodide (900 mg, 3.25 mmol, in 10 mL of benzene) was added. The mixture was stirred under argon for 36 hours at 60° C. The precipitate was removed by filtration and the filtrate was evaporated to dryness. The residue was then dissolved in CH$_2$Cl$_2$ and resolved by chromatography on silica (hexane:EtOAc, 5:1 to 2:1 as eluant) to give the product as yellow solid.

Example 6

Coupling to give O-protected 6-amino-5-nitro-3-(1'-beta-D-2'-deoxyribofuranosyl)-2(1H)-pyridone, also known as 6-amino-3-(2'-deoxy]-D-ribofuranosyl)-5-nitro-1H-pyridin-2-one, or 6-amino-3-{3'-[(1,1-dimethylethyl)diphenylsilyloxy]]-D-glycero-pentofuran-3'-ulos-1'-yl}-5-nitro-1H-pyridin-2-one A suspension of palladium acetate (7 mg, 0.031 mmol) and triphenyl arsine (19 mg, 0.061 mmol) in DMF (2 mL) was stirred at room temperature for 30 min, to give in yellow suspension. A solution of 6-O-(2-p-nitrophenylethyl)-2- amino-3-nitro-5-iodopyridine (88 mg, 0.204 mmol) and the 3-TBDPS-5-unprotected unsaturated sugar derivative from above (109 mg, 0.307 mmol) was prepared in DMF (3 mL) and dried overnight over molecular sieves (4 Å). This solution was added to the yellow suspension, followed immediately by addition of triethylamine (0.06 mL, 0.408 mmol). The suspension was stirred at 55° C. for 2 days. The solvent was removed under high vacuum. The residue was suspended in $CH_2Cl_2$ (60 mL), the insoluble material removed by filtration and the organic solution evaporated. Column chromatography on silica (hexane:EtOAc=2:1 to 1:1.5 as eluant gave the coupled product, with some of the TBDPS removed. Therefore, the mixture was reduced rapidly (net step).

Reduction of the Ketone

Sodium triacetoxyborohydride (0.549 g, 2.475 mmol) was added in one lot to a solution of the product of the previous step (1.65 mmol) in acetonitrile (8 mL) and acetic acid (4 mL) under an Ar atmosphere. TLC (ethyl acetate) indicated that there was no starting material after 12 min. The reaction was quenched by the addition of acetone, and the reaction mixture concentrated under reduced pressure. The resulting pale yellow gum was dissolved in methanol, adsorbed onto silica, and purified by flash chromatography (ethyl acetate) to give the desired material as a white solid.

Example 7

Figure 1:
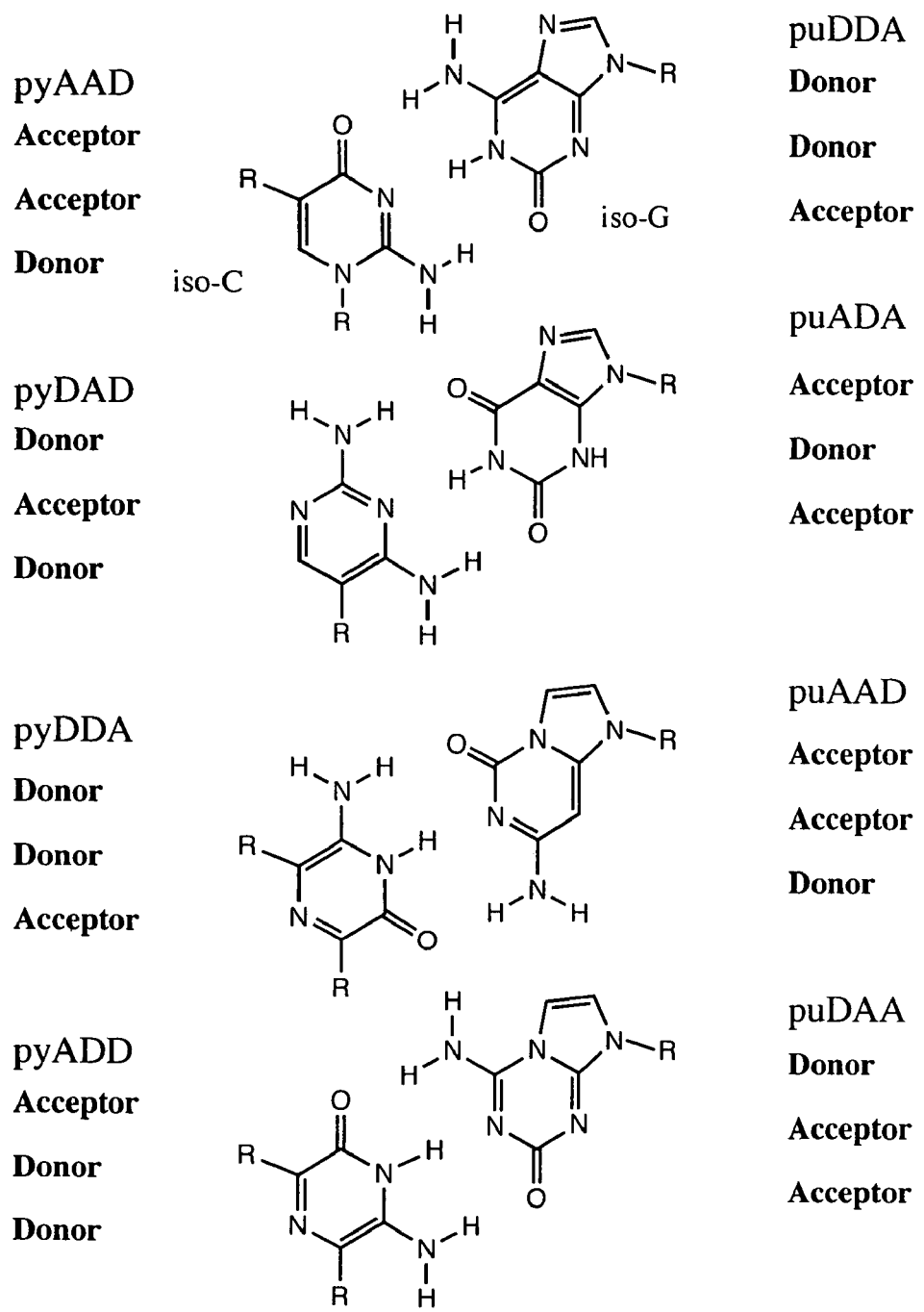
FIG. 1. From U.S. Pat. No. 6,140,496, the specific compositions of matter used to implement different hydrogen bonding patterns of the expanded genetic alphabet.
Figure 2:
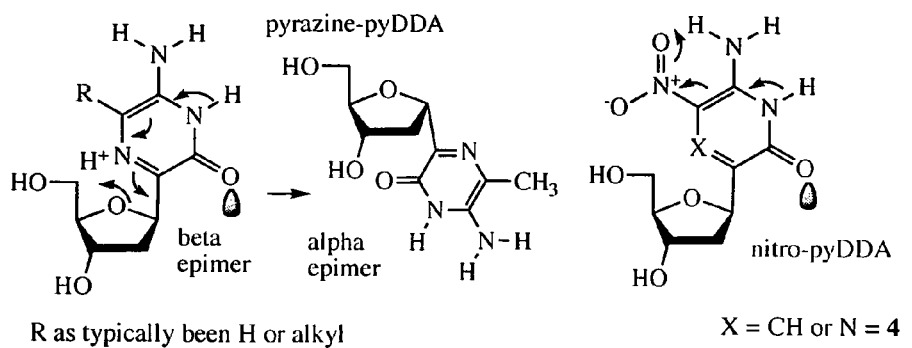
FIG. 2. The epimerization mechanism for the pyrazine heterocyclic systems that are proposed in the art to implement the pyDDA and pyADD hydrogen bonding patterns.
Figure 2:
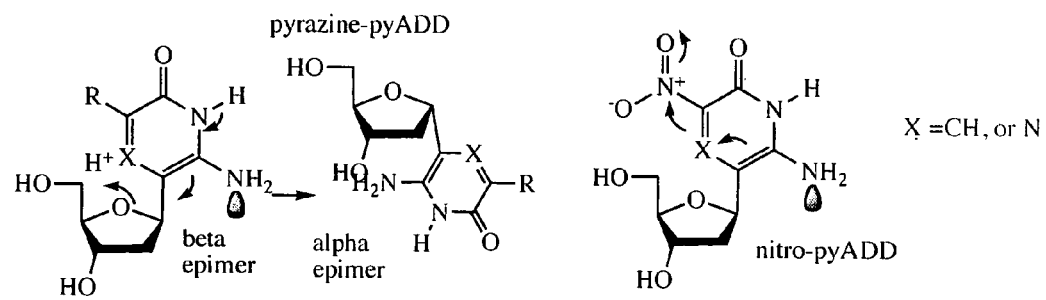

Formation of 2,6-diamino-5-nitro-3-(1'-beta-D-2'-deoxyribofuranosyl)-pyridine, implementing the pyDAD hydrogen bonding pattern Conversion of the O-NPE Unit into an Amino Group The product of the previous step was dissolved in a 1:1 mixture of dioxane and 29% ammonia in water. The mixture was heated for 2 days at 55 C. The product was 2,6-diamino-3-nitro-5-(1'-beta-D-2'-deoxyribofuranosyl)-pyridine(compound 1 in FIG. 2).

Example 8

Making a Protected Derivative of the pyDAD Nucleoside of the Instant Invention Suitable for Use in Automated DNA Synthesis Protection 2,6-Diamino-5-nitro-3-(1'-beta-D-2'-deoxyribofuranosyl)-pyridine (8 mmol) was dissolved in anhydrous pyridine (40 mL) together with some 4-dimethylaminopyridine (5 mmol). The anhydride of phenoxyacetic acid (130 mmol) was added in one lot to a stirred mixture of the product from above (2.008 g, 8 mmol) and DMAP under Ar. The mixture was stirred for 18 h. Triethylamine (16 mL) was then added, and the vessel was cooled in an ice/water bath. Ethanol (32 mL) was slowly added to the mixture.

The mixture was then concentrated under reduced pressure, and the resulting solid was partitioned between dichloromethane (50 mL) and water (50 mL). After removing the aqueous phase, the organic solution was washed with water (2×50 mL), dried ($MgSO_4$), filtered, and the filtrate concentrated under reduced pressure to give crude material. Purification by flash chromatography (1:3 ethyl acetate:hexanes) gave the desired material as a pale yellow solid. The protection groups were then removed from the alcohol groups by treatment with 1 N NaOH in water:dioxane mixtures at room temperature for 30 min to give the 2,6-bis(phenoxyacetylamino)-3-nitro-5-(1'-beta-D-2'-deoxyribofuranosyl)-pyridine.

Tritylation

The protected nucleoside analog (8.7 mmol) was dissolved in dry pyridine (150 mL). To the solution was added 4',4''-dimethoxytrityl chloride (1.2 equiv). The reaction mixture was stirred at room temperature for 24 hours. The reaction was quenched by the addition of water (3 mL). The solution was concentrated under vacuum, and an aqueous solution of $NaHCO_3$ (80 ml) was added. The mixture was extracted with EtOAc, dried ($Na_2SO_4$), the solvents were evaporated under reduced pressure, and the product was isolated by column chromatography (chloroform/acetone 9:1, then 9:2).

Phosphoramidite.

The protected derivative from above (0.12 mmol) was dissolved in $CH_3CN$ (2.0 mL). The solution was then treated with bis-(N,N-diisopropylamino)-3-cyanoethyloxyphosphine (Aldrich, 1.2 equiv.), and diisopropylammonium tetrazolide (0.06 mmol), following a literature procedure [McBride, L. J., Kierzek, R., Beaucage, S. L. & Caruthers, M. H. (1986) *J. Am. Chem. Soc.* 108, 2040-2048]. The progress of the reaction was monitored by TLC ($SiO_2$ eluted with EtOAc:$CH_2Cl_2$:triethylamine 45:45:10). An additional portion (0.02 mL) of bis-(N,N-diisopropylamino)-3-cyanoethyloxyphosphine was then added, and stirring continued for an additional hour. Water (2 drops) was added, the mixture stirred for 15 min, the mixture diluted with $CH_2Cl_2$ (30 mL), and the organic layer washed with aqueous $Na_2CO_3$ (2%) and dried ($Na_2SO_4$). The phosphoramidite (120.3 mg, 93%) was isolated by chromatography ($SiO_2$, EtOAc:$CH_2Cl_2$:triethylamine 45:45:10 as eluant).

Example 9

Synthesis of the Triphosphate

3'-O-(Acetyl) derivative of the nucleoside analog

The dimethoxytritylated nucleoside analog from above (0.200 mmol) was coevaporated with dry pyridine (0.8 mL). The residue was redissolved in pyridine (1 mL) under dry Ar. Acetic acid anhydride (10 equiv) was added dropwise, and the reaction mixture was stirred for 3 h. The solution was then cooled on an ice bath, and the reaction was quenched by addition of methanol (1 mL). The solvents were evaporated under reduced pressure. The remaining foam was coevaporated with dry toluene (1 mL), and the residue was dissolved in a mixture of trifluoroacetic acid and $CH_2Cl_2$ (2% v/v, 10 mL total volume). The mixture was then stirred for 30 min, at which point saturated aqueous $NaHCO_3$ solution (5 mL) was added. The phases were separated, the aqueous phase isolated, and the aqueous phase extracted with $CH_2Cl_2$. The combined organic phases were concentrated under reduced pressure, and the remaining yellowish oil was resolved by chromatography on silica gel ($CH_2Cl_2$/MeOH 98:2) to afford the 3'-O-acetyl derivative of the nucleoside, with its 5'-OH group free.

5'-O-Triphosphate derivative of the nucleoside analog

The 3'-acetylated nucleoside analog (0.162 mmol) was then coevaporated again with dry pyridine (1 mL). The residue was then redissolved in a mixture of dry pyridine (162 μL) and dry 1,4-dioxane (486 μL) under Ar. A freshly prepared solution of 2-chloro-4H-1,3,2-benzodioxaphosphorin-4-one (1 M) in 1,4-dioxane (162 μL, 1.0 equiv) was then added to the stirred reaction mixture. A white precipitate formed immediately. After 10 minutes, a well vortexed emulsion of tributylammonium pyrophosphate (110 mg) in DMF/tri-n-butylamine (3:1, 648 µL) was quickly added. This caused the precipitate to dissolve immediately.

After 10 minutes of incubation at room temperature, a 1% solution of iodine in pyridine/water (98:2, 3.24 mL) was added dropwise. After 15 min following completed addition of the iodine solution, the solvents were removed at 40° C. under reduced pressure. The remaining brown oil was dissolved in water/MeOH (1:1, 10 mL), and the mixture was allowed to stand for 30 minutes. Then, a portion of solution of aqueous concentrated ammonia (20 mL) was added; the solution turned turbid. The suspension was stirred for 1 h, the solvents were removed at 40° C. under reduced pressure, and the remaining light brown oil was coevaporated with water.

Water/acetonitrile (95:5, 2 mL) was then added to yield a light brown suspension. The unsoluble components were removed by filtration (0.2µ a cellulose acetate membrane) to yield a clear, slightly yellow, filtrate containing the triphosphate. The triphosphate was purified by chromatography (DEAE Sephadex, 30 mL, 1.5×18 cm; TEAB 0.1 M to 0.8 M (linear gradient) in the presence of 10% acetonitrile). Further purification was done by reversed phase RP-HPLC (Column: Nova-Pak HR C18 cartridge (Waters), 6µ, 25×100 mm. Solvent A: triethylammonium acetate (25 mM, pH 7.0); solvent B: acetonitrile. Flow rate: 5.5 mL/min. Gradient: 0-1 min 100% A; 10 min 13% B (linear); 55 min 18% B (linear)). The eluate was lyophilized to dryness, and the residue was redissolved in water. Dissolution and lyophilization was done three more times, to remove the residual triethylamonnium acetate. The triphosphate was stored at −20° C., either as 5 mM solution in water or as a lyophilized powder. The triphosphate was recognized by characteristic signals in the $^{31}P$ NMR in $D_2O$ solvent (121 MHz: δ relative to phosphoric acid=−7.9 (poorly resolved doublet), −9.1 (doublet), and −20.6 (triplet) ppm).

Example 10

Chemical Synthesis of Oligonucleotide Analogs Incorporating the Disclosed Nucleoside Analog Oligonucleotide analogs containing non-standard nucleotide were prepared by "trityl off" solid-phase synthesis using an Applied Biosystems automated DNA synthesizer from the β-cyanoethyl protected phosphoramidites. The oligonucleotides were purified by polyacrylamide gel electrophoresis (12-20%). Chemicals were purchased from Glen Research. DNA membrane columns (0.2 µmol scale) and CPG columns (1.0 µmol scale) containing the 3'-terminal nucleoside were purchased from PerSeptive Biosystems.

Vials to contain the protected phosphoramidite of the nucleoside analog were rinsed with acetone and immediately placed into an oven at 150° C. to dry overnight. The vials were then cooled to room temperature in a dessicator over $P_2O_5$ under vacuum of <1 torr. The dessicator was vented with dry Ar, and phosphoramidite was placed into the vials. If only a small amount of phosphoramidite was available, the compound was transferred into the prepared vial as solution in $CH_2Cl_2$, and the solvent was evaporated under reduced pressure. Subsequently, the vials containing the phosphoramidites were returned to the desiccator with $P_2O_5$ to be stored under vacuum. The desiccator was vented with dry Ar, and the vials were immediately closed and stored in a dessicator containing anhydrous $MgSO_4$ until needed.

Directly before oligonucleotide synthesis, the phosphoramidites were dissolved in anhydrous acetonitrile (0.15 g/1.5 mL). Standard phosphoramidites were used as solutions in anhydrous acetonitrile (0.5 g/10 mL) at half the concentration that was recommended by the synthesizer manufacturer. Synthesis on a 0.2-1.0 µmol scale was performed using a standard synthesis protocol, with the exception of an extended coupling time (600 s) for the analog.

After the synthesis was complete (0.2-1.0 µmol scale), the column material (CPG beads) was transferred into a 1.5 mL microcentrifuge tube with sealed screw cap. Upon addition of concentrated $NH_4OH$ solution (1 mL), the tube was shaken overnight at 55° C. in an Eppendorf shaker at maximum speed. After the mixture had been centrifuged for a few seconds, the supernatant was transferred into a clean microfuge tube. The column material was washed with water (250 µL), and the wash supernatant was combined with the first supernatant. The solvent was evaporated from the combined supernatants by means of a speed vac at ambient temperature. The residue was dissolved in NaOAc solution (0.7 M, pH 5.2; 300 µL). An occasionally occurring cloudy precipitate was removed by filtration through a syringe filter with cellulose acetate membrane (pore size 0.2 µm). Ice cold EtOH (1 mL) was added to the clear solution. After vortexing, the mixture was stored at −20° C. for several hours. The mixture was then centrifuged at 4° C. and 14,000 rpm for 30 min, and the supernatant was removed. The remaining pellet was washed with 80% aqueous EtOH (1 mL) by gentle shaking, and the mixture was centrifuged again at 4° C. and 14,000 rpm for 10 min. After removal of the supernatant, the oligonucleotide pellet was dried by exposure to the air and redissolved in water (500 µL).

The oligonucleotide analog (purified by either HPLC or that was obtained after above described post synthetic processing) was mixed with PAGE loading buffer (1:1). The mixture was incubated at 95° C. for 2 min and immediately loaded onto the preheated polyacrylamide gel. Up to ¼ of a 0.2 µmol synthesis or 1/20 of a 1.0 µmol synthesis was loaded into one well. Electrophoresis was performed at 45-55 W, maintaining a gel temperature of 55-60° C. When the desired oligonucleotides had migrated about 25 cm, as judged by the dye markers, electrophoresis was stopped. The oligonucleotide bands were visualized by UV quenching with the help of a silica gel coated TLC plate containing a fluorescence indicator. The desired bands were cut out with a razor blade. Usually the slowest migrating band of a crude mixture corresponded to the desired full length product. The gel pieces were transferred into tubes of appropriate size and crushed with the help of a pipette tip. NaOAc solution (300 mM, pH 7.5) was added to completely cover the gel particles. The mixture was shaken vehemently on a vortexer for 5 h to overnight. After centrifugation, the supernatant was removed. The gel particles were shaken with a fresh portion of NaOAc solution (300 mM, pH 7.5) for a few hours. The supernatant was filtered and combined with the supernatant from the first extraction. The combined supernatants were filtered through a cellulose acetate membrane (pore size 0.2 µm). The oligonucleotide was recovered from the filtrate by EtOH precipitation. The pellet was washed with 70% EtOH. The so obtained oligonucleotides were pure enough for all subsequent applications and were stored as solutions in water (3-250 pmol/µL) at −20° C.

The concentrations of the oligonucleotide solutions were determined via measurement of the UV absorbance of the oligonucleotide solution at λ=260 nm.

The relation between UV absorbance and the amount of the oligonucleotide (in nanomoles) present in the sample was given approximately by the formula $A_{260}*100/n$=nmole oligonucleotide, where $A_{260}$ is the absorbance at λ=260 nm in OD, and n was the number of bases of the oligonucleotide.

This formula was employed for both standard and functionalized oligonucleotides without consideration of the extinction coefficient of the functionalized bases.

Oligonucleotide analogs were analyzed by anion exchange HPLC under the following conditions:
Column: Dionex
Solvent A: Sodium phosphate (20 mM, pH 6.0); solvent B: Sodium phosphate (20 mM, pH 6.0), NaCl (1 M); solvent C: ACN.
Gradient: 0-1 min 75% A/25% C; 30 min 55% B/25% C (linear).

For purification of large amounts of oligonucleotides (up to 10 OD), a larger column with the same packing material was used. The gradients were adjusted to keep the Room temperature value about constant. On the preparative scale, the oligonucleotides were further purified and desalted on a larger column (NOVA PAK HR C18 cartridge (Waters), 6 μm60 Å, 25×100 mm; flow rate 5.5 mL/min).
Chromatography Times were Extended by 5 Min.

Oligonucleotides containing the nucleotide analog were characterized by MALDI-TOF mass spectrometry. Short oligonucleotides (9-10mers) were also analyzed by electrospray ionization mass spectrometry (ESI MS). The oligonucleotide was injected as solution in isopropanol/water (1:1) containing TEA (30 mM).

The oligonucleotide analogs were further analyzed by enzymatic degradation. The analog was dissolved in water/acetonitril mixtures (9:1, 4.0 μL). Digestion buffer (0.1 M Tris-HCl, pH 8.3, 20 mM $MgCl_2$; 4.0 μL) and 10 mM Zn $(OAc)_2$ solution (1.0 μL) was then added, followed by phosphodiesterase I (1.0 μL, 0.0006 U), nuclease P1 (1 μL, 0.0006 U) and alkaline phosphatase, diluted with digestion buffer (1.0 μL, 1.5 U). The mixture was incubated at 50° C. for 5 h. The sample was then diluted with triethylammonium acetate buffer (1 M, pH 7.0, 20 μL) and water/acetonitrile (9:1, 70 μL), filtered and analyzed using RP-HPLC (Column: Adsorbosphere, Solvent A: TEAOAc (25 mM, pH 7.0); solvent B:solvenacetonitrile 4:1; solvent C: acetonitrile. The composition of the oligonucleotide was verified by using the integrated absorbance of the component nucleosides at 260 nm.

Example 11

Structures Having Utility

A molecular beacon containing the disclosed nucleoside analog and its complement in the stem,
Fl-5'-YTYYRTGTGTTTTCTACAAGCTGATGYR-RAR-3'-Qu (SEQ ID NO: 1)

Y and R represents the nucleoside analog implementing either the pyDDA:puAAD, pyADD:puDAA, or pyDAD:puADA hydrogen bonding patterns, incorporated into a DNA strand. Y and R were complementary. Thus, the large 5-6 fused ring system that presents a puAAD or puDAA (respectively) hydrogen bonding patterns were preferably 2-amino-1,9-dihydro-5-aza-7-deaza-9-(1'-beta-D-2'-deoxyribofuranosyl)-1H-purin-6-one, and 4-amino-8-(2-deoxy-beta-D-erythro-pentofuranosyl)-imidazo[1,2-a]-1,3,5-triazin-2 (8H)-one, respectively. A, T, G, and C represent the 2'-deoxyribonucleotides as generally disclosed in the literature. Fl is preferably a fluorescent moiety, in this example rhodamine. Qu is preferably a fluorescence quencher moiety, here DABCYL.

An oligonucleotide analog suitable for immobilization using avidin analogs.
5'-biotin-YTYYRTGTGTTTTCTACAAGCTGATG (SEQ ID NO: 2)

where Y and R are as defined above, A, T, G, and C represent the 2'-deoxyribonucleotides as generally disclosed in the literature. Fl is a fluorescent moiety. Qu is a fluorescence quencher moiety. This is able to mediate the capture of the following oligonucleotide to a solid support, which may be a two dimensional array, a one dimensional array, or a bead:
3'-RARRYACACAAAAGATGTTCGACTA-CAAAAAAGA (SEQ ID NO: 3)

The process of the capture is performed at room temperature in phosphate buffer (0.1 mM, pH 7.0) in the presence of NaCl (500 mM).

A Primer-Template Combination.
5'-YTYYRTGTGTTTTCTACAAGCTGATG-3' (primer) (SEQ ID NO: 4)
3'-ACACAAAAGATGTTCGACTA-CAAAARYGACTTGTACAT-5' (template) (SEQ ID NO: 5)
where Y and R are as defined above.

Example 12

Enzymic Synthesis of Oligonucleotide Analogs Containing the Disclosed Nucleoside Analog Under the Direction of a Template Primer Extension Experiments.
In a typical primer extension experiment, 5'-$^{32}$P-labeled primer having the sequence shown below:
5'-YTYYRTGTGTTTTCTACAAGCTGATG-3' (primer) (SEQ ID NO: 4)
3'-ACACAAAAGATGTTCGACTA-CAAAARYGACTTGTACAT-5' (template) (SEQ ID NO: 5)
where Y and R were as defined above, and A, T, G, and C represent the 2'-deoxyribonucleotides as generally disclosed in the literature.

The template, in this example, has the sequence shown above (656 nM of the primers, 920 nM of the templates). The reaction is run in the buffer appropriate for the polymerase or reverse transcriptase supplier (sold by the polymerase or reverse transcriptase supplier). Here, the polymerase is Therminator from New England Biolabs. The components are mixed with dATP, dGTP, dCTP, TTP and dQTP (Q was the nucleoside analog, either R or Y, all triphosphates at a final concentration 130 μM each) in a total volume of 160 μL. After heating the mixture to 95° C. for 1 min, the primer/template complex is annealed by cooling slowly to room temperature over 1 h. Primer extension is started by addition of the polymerase (16 μL). The mixture is then incubated at the optimal temperature for the polymerase. Aliquots (25 μL), taken at various times during the elongation reaction, are quenched by addition of a premixed solution of sodium acetate (2.5 μL, 3 M, pH 5.2), EDTA (1 μL, 0.5 M, pH 8), and ethanol (50 μL). After being stored at −20° C. for 20 min, the samples are centrifuged (14,000 rpm, 4° C., 20 min) and the pellets dried in the vacuum concentrator. The residues are redissolved in PAGE loading buffer and the samples separated on a 10% PAGE gel (7 M urea). The gel was analyzed using the MOLECULARIMAGER.

To improve reproducibility in cases where multiple reactions are run in parallel, a master mixture of primer/template and the dNTPs is prepared by scaling up the listed procedure. Master mixtures are not stored for more than 24 hours at −20° C.

Standing Start Experiments.
The primer (15 pmol, 5'-$^{32}$P-labeled) and template (21 pmol) are incubated with polymerase at the conditions specified by the supplier, with the volume adjusted with water to 21 μL with water. The DNA is denatured (95° C., 1 min) and cooled to room temperature over a period of 1 hour. After addition of the appropriate dNTPs (1.67 µL, 130 µM final concentration of each) and an aliquot of Taq polymerase (0.2 U), the mixture is incubated for up to 30 min at 37° C. The reaction is quenched by addition of a premixed solution of sodium acetate (2.5 µL, 3 M, pH 5.2), EDTA (1 µL, 0.5 M, pH 8), and EtOH (50 µL), the DNA was recovered by centrifugation, and the pellet was dried in the vacuum concentrator. The DNA is dissolved in PAGE loading buffer (bromophenol blue/xylene cyanol mix 0.1 g, water, 1 mL, and formamide, 4 mL) and analyzed using a 10% PAGE gel (7 M urea). The gel is analyzed with the MOLECULARIMAGER.

Example 13

Enzymic Synthesis of a Library of Random Sequence Oligonucleotide Analogs Containing the Non-Standard Nucleotide Using Terminal Transferase, not Under the Direction of a Template

| In a 1.5-ml Eppendorf-tube was added: | |
|---|---|
| 1. Water | 642.0 µL |
| 2. Cacodylate buffer (5x conc.) | 200.0 µL |
| 3. MgCl$_2$ (100 mM) | 80.0 µL |
| 4. CoCl$_2$ (100 mM) | 40.0 µL |
| 5. dNTP-Mix (each 10 mM dATP, dCTP, dGTP, TTP, and dQTP) | 25.0 µL |

The final concentration of each triphosphate is 0.25 mM; there was in total 1 mM triphosphate.

| | | |
|---|---|---|
| 6. Seq1 (20) (113 pmol/µL; = total 1 nmol) | 8.9 | µL |
| 7. Terminal transferase (25 units/µL; = total 100 units) | 4.0 | µL |

The sodium cacodylate-trihydrate buffer was prepared by dissolving (2.14 g, 10 mmol) in ca. 5 ml of water. Tris.HCl buffer (1.25 mL; 1.0 M, 8.0), 1.25 mL acetylated bovine serum albumin (10 mg/ml, New England Biolabs) and water were mixed to a final volume of 10 mL. The pH was adjusted at 6.6 by adding a few drops of concentrated HCl and the stock solution sterilized by ultrafiltration. The mixture was stored at −20° C.

Prior to the reaction mixture was shaken briefly and incubated for 16 hours at 37° C. In the beginning the solution was clear; a white precipitate was observed to form, presumably cobalt pyrophosphate. To stop the reaction, the tube was placed on ice and diluted with 0.1 volume of an EDTA solution (200 mM in water, pH=8). The reaction mixture was divided into four Eppendorf tubes and the DNA was precipitated with ethanol (addition of 0.11 volumes of 3.0 M NaOAc, pH=5.4 and 2.5 volumes of ethanol. The mixture was stored at −20° C. overnight, centrifuged at 4° C. for 30 min, the supernatant was removed by pipette and discarded. The precipitate was washed with 500 µl of 70% ethanol, dried for 2 hours in air at room temperature, and dissolved in 100 µl water to yield a solution of ≦1 nmol DNA "Seq 1-random" in 400 µl water.

The DNA oligos were analyzed by agarose gel electrophoresis (2% agarose in TAE-buffer, ethidium bromide) usnig pBR 322 MspI-digestion as markers. The sample consisted of 5.0 µl DNA-solution (≦1 nmol 21 in 400 µl water) plus 1.0 µl gel loading buffer III (6× conc.). The gel was developed (30 min, 76 V), and visualized under ultraviolet light (1λ=254 nm). The gel of the mixture of oligodeoxyribonucleotides 21 displayed (as expected) no sharp bands, but rather a "smeared" band with a center at ca. 300 nt, and visibly extending from 200 to 600 nt.

Example 14

Immobilization of an Oligonucleotide Analog Incorporating the Disclosed Nucleoside Analog onto a Microsphere, or Bead The process is illustrated by FIG. 4.

Example 15

Figure 5:
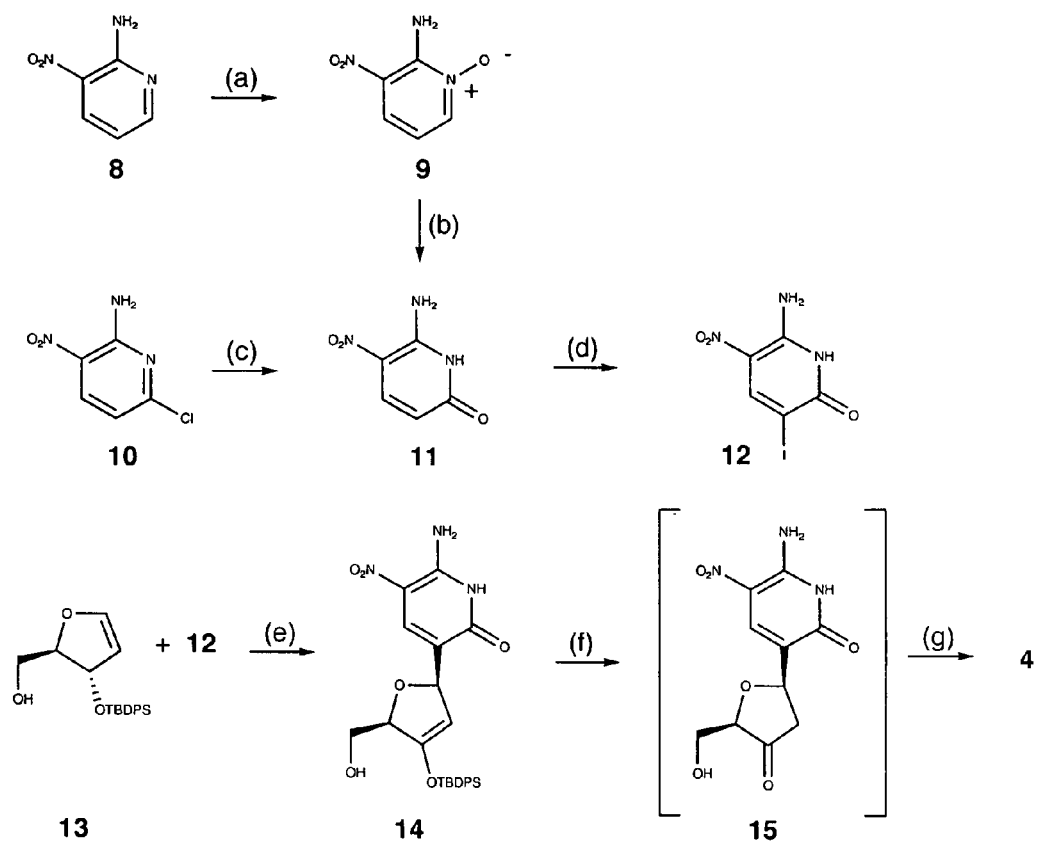
FIG. 5. Schematic showing the synthesis of one implementation of the pyDDA hydrogen bonding pattern. The pyADD implementation is synthesized analogously, from the appropriate different iodinated heterocycle. Key: (a) mCPBA, acetone, rt; (b) 1) KOAc, $Ac_2O$, Δ, 2) MeOH—$NH_3$, rt; (c) NaOH, EtOH/$H_2O$, Δ; (d) N-iodosuccinimide, DMF, rt; (e) cat. $Pd(OAc)_2$-$2Ph_3As$, $Et_3N$, DMF, 60° C.; (f) TBAF, THF, 0° C.; (g) $NaBH(OAc)_3$, MeCN/MeCOOH, 0° C. Corresponding schemes can be envisioned by one of ordinary skill in the art for the ribonucleoside analog, and for various analogs with various sugar derivatives and sugar analogs.
Figure 6:
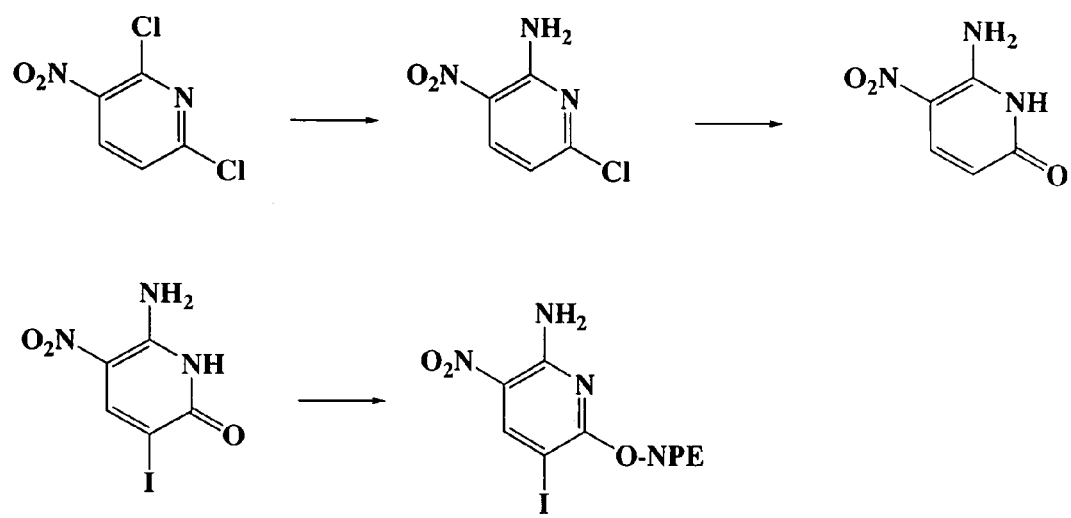
FIG. 6. Schematic showing the synthesis of the iodoheterocycle precursor of the pyDDA and pyDAD, with the NPE protecting/activating group.
Figure 7:
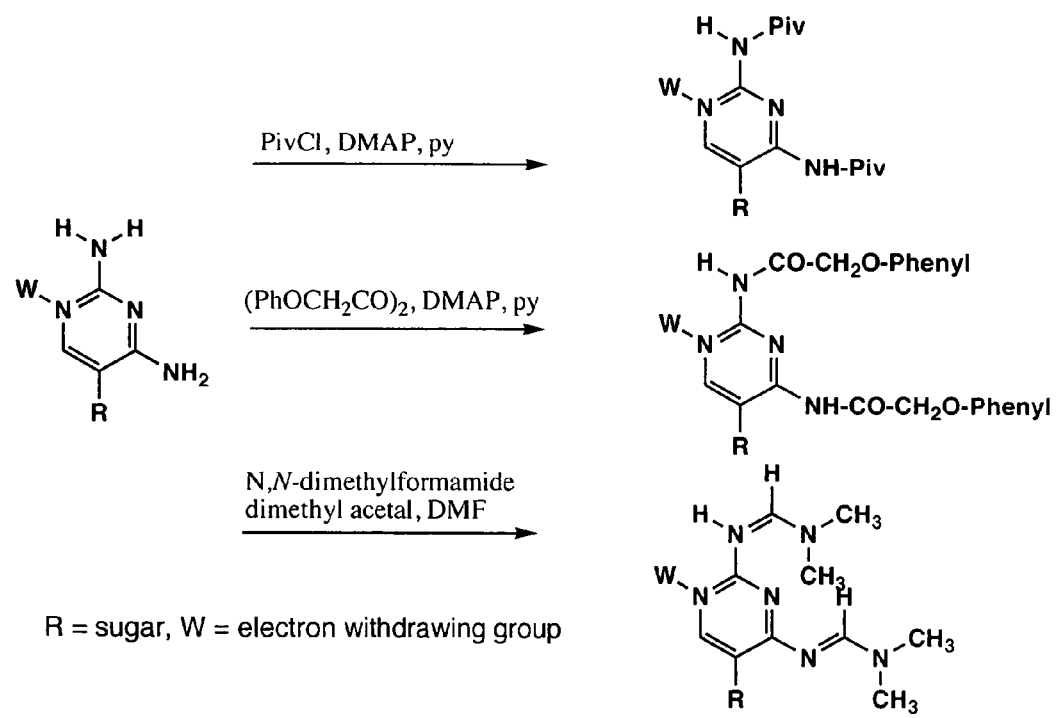
FIG. 7. Schematic showing the protection of the heterocycles that serve as precursors of the nucleoside analog of the instant invention. Analogous processes protect the exocyclic amino groups of the precursors of the pyDDA and pyADD analogs, suitable for DNA synthesis.
Figure 8:
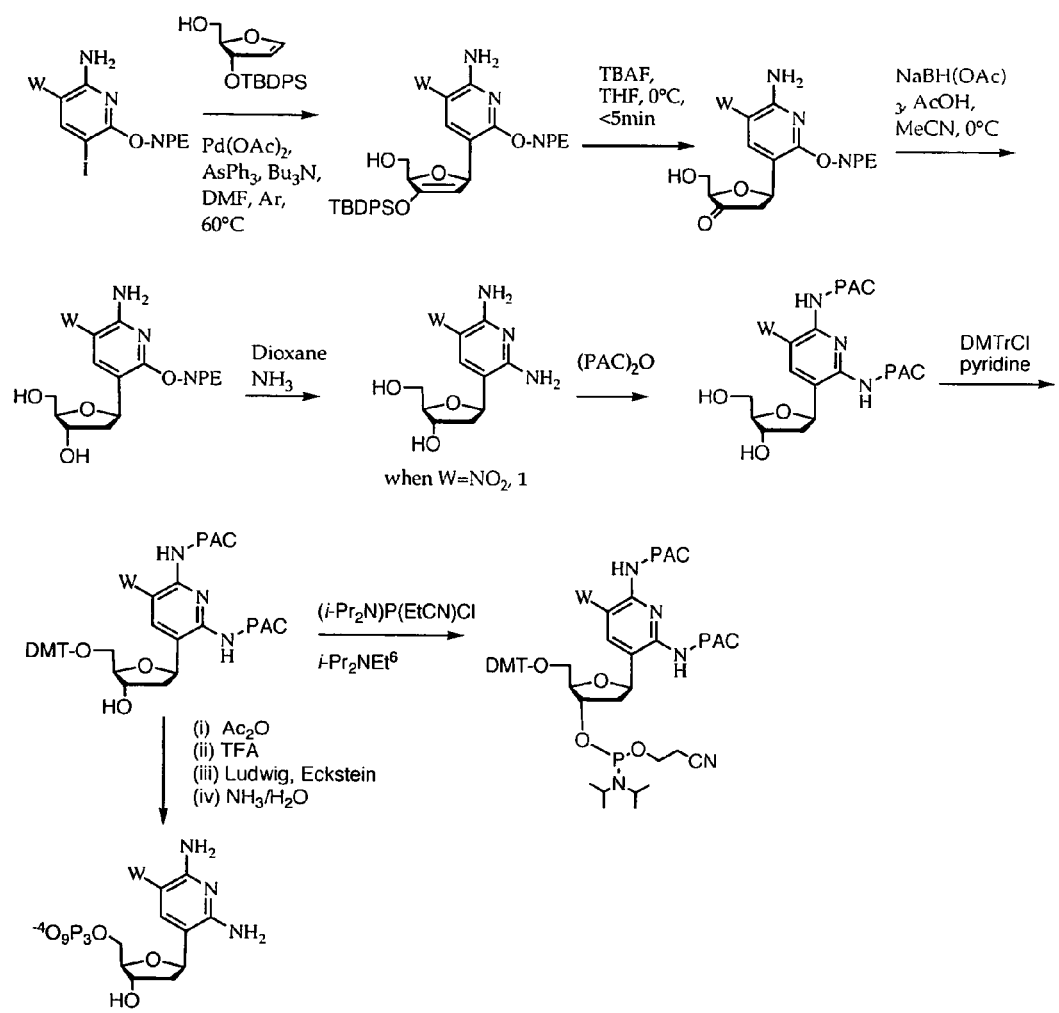
FIG. 8. Schematic showing the coupling to give the nucleoside analogs of the instant invention, in a form that leads to either the pyDAD implementation or the pyDDA implementation, together with the formation of the protected derivatives suitable for oligonucleotide synthesis, and triphosphate synthesis.
Figure 9:
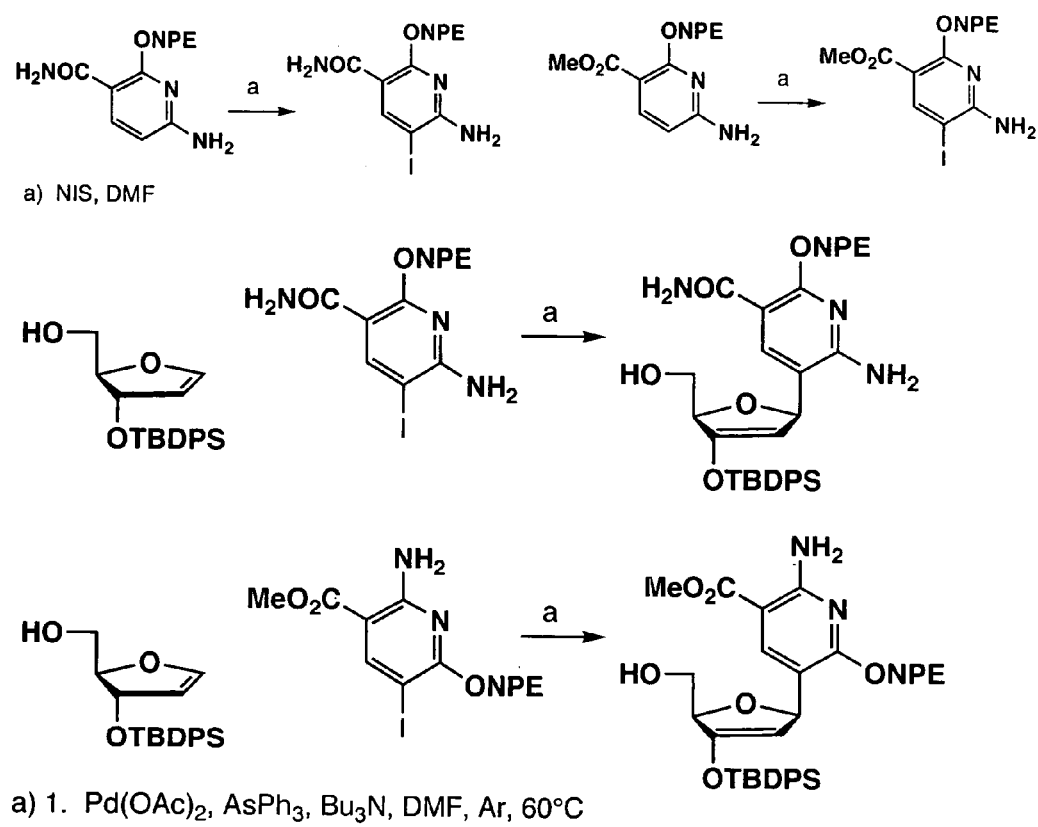
FIG. 9. Schematic showing synthesis of pyDDA and pyAAD with carboxylate electron withdrawing groups.

Process of Using Oligonucleotide Analogs Containing the Disclosed Nucleoside Analog for the Purpose of Binding to a Complementary Nucleotide Analogs The process is illustrated by FIGS. 4 and 5.

Example 16

Immobilization of an Oligonucleotide Analog Incorporating the Disclosed Nucleoside Analog onto a Two Dimensional Array The process is illustrated by FIGS. 4 and 5, where the support is a two dimensional array. Analogous processes use a one dimensional array, a Luminex bead, a magnetic microsphere, or a quantum dot as the solid support.

Example 17

Amplification of an Oligonucleotide Analog Incorporating the Disclosed Nucleoside Analog in a Polymerase Chain Reaction To facilitate strand separation, one of the PCR primers (P2-C6) was designed to contain a tetranucleotide appended to the 5'-position via two C6 polyethyleneglycol units. This made the product derived from the primer move slower in a gel electrophoresis experiment than the product derived from the reverse primer.

Template T2-pyDAD (50 pmol) was mixed with 5'-radiolabeled primer P2-C6 (750 pmol), primer P1-RS (750 pmol), dATP, dTTP, dCTP, dGTP, d(puADA)TP, d(pyDAD)TP (final conc. 200 µM each), HIV reverse transcriptase buffer (333 µL, 3×), and the reaction volume adjusted to 1 mL with water. The mixture was heated to 95° C. (10 mi) and allowed to cool to ambient temperature (1 h). A mutant HIV reverse transcriptase (Y188L,E478Q) (10 U) was added to the reaction mixture, which was then incubated at 37° C. for 24 hours. An aliquot (5 µL) was removed and quenched with 20 mM EDTA in formamide (5 µL). The remaining reaction mixture was heated again to 95° C. for 10 minutes and again cooled to ambient temperature over 1 hour. Another aliquot of reverse transcriptase was then added. This cycle was repeated 4 times. The products from each round of PCR amplification were resolved using a 12% PAGE gel (7 M urea). The gel was analyzed using the MolecularImager software. A positive control experiment was run under the same conditions while substituting T-2 for T2-pyDAD.

The PCR reaction was quenched with EDTA (final conc. 10 mM) and the DNA isolated via ethanol (2.5 mL) precipitation and subsequently washed with 70% ethanol in water. The dry pellet was dissolved in PAGE loading buffer and analyzed by electrophoresis on a 20% PAGE gel (7 M urea). The product generated from full extension of primer P2-C6 was longer, and therefore moved slower, than the product generated from the full extension of P2-Rev. The product from full extension of P2-C6 was cut from the gel and extracted by incubating in a crush and soak buffer (0.1% SDS, 0.5 M $NH_4OAc$, 10 mM $Mg(OAc)_2$) at 37° C. overnight. The solution was filtered through a Millipore filter (0.45 μm pore size) and the DNA recovered by ethanol precipitation. The DNA pellet (T1-X-PCR) was dissolved in water to a final concentration of 10 μM.

Example 18

Incorporation of the Disclosed Nucleoside Analog into a Dendrimeric Structure Based on Branched DNA The process is illustrated by FIGS. 4 and 5, following literature in the prior art for oligonucleotide analogs that do not incorporate the nucleoside of the instant invention. [Collins, M. L.; Irvine, B.; Tyner, D.; Fine, E.; Zayati, C.; Chang, C. A.; Horn, T.; Ahle, D.; Detmer, J.; Shen, L. P.; Kolberg, J.; Bushnell, S.; Urdea, M. S.; Ho, D. D. Nucl. Acids Res. 1997, 25, 2979-2984.]

Example 19

Incorporation of the Disclosed Nucleoside Analog into a Dendrimeric Structure that Incorporates Non-Nucleosidic Components Oligonucleotide analogs synthesized as described above are incorporated into DNA dendrimers, following the procedure disclosed in the literature, where this literature disclosure does not describe dendrimers with containing the nucleoside analog of the instant invention, but rather is constructed from all standard nucleotides. [Lowe, M, Spiro, A, Zhang, Y Z, Getts, R (2004) Multiplexed, particle-based detection of DNA using flow cytometry with 3DNA dendrimers for signal amplification. *Cytometry Part A* 60A (2): 135-144][Wang, J, Jiang, M, Nilsen, T W, Getts, R C (1998) Dendritic nucleic acid probes for DNA biosensors. *J. Am. Chem. Soc.* 120 (32): 8281-8282][Hudson, R H E, Robidoux, S. Damha, M J (1998) Divergent solid-phase synthesis of nucleic acid dendrimers. *Tetrahedron Lett.* 39 (11): 1299-1302][Hudson, R H E, Damha, M J (1993) nucleic-acid dendrimers. Novel biopolymer structures. *J. Am. Chem. Soc.* 115 (6): 2119-2124].

These are used in a multiplexed, flow cytometric assay, using fluorescence detection. The analyte consists of single-stranded (ss) DNA amplicons that are hybridized to capture probes on the surface of fluorescent polystyrene microspheres (beads) and that are labeled with streptavidin-R-phycoerythrin (single-step labeling). These beads have a low reporter fluorescence background and high efficiency of DNA hybridization. The DNA/SA-RPE complex is then labeled with dendrimers and SA-RPE. The bead complexes were detected with a Luminex 100 flow cytometer. Bead standards are developed to convert the intensity to the number of SA-RPE labels per bead and the number of dendrimers per bead.

The purifications are carried out under an argon atmosphere. Solvents for water sensitive reactions are dried over 3-Å molecular sieves, $Et_3N$ was distilled over $P_2O_5$. NMR: $_1H$ at 300 MHz and $^{13}C$ at 75 MHz; ppm in ppm; calibration to $SiMe_4$($^1H$) or residual solvent peak ($^{13}C$). Reverse phase HPLC: preparative: Waters Prep Nova-Pak® HR $C_{18}$ Cartridge (60 Å, 25°-100 mm), analytical: Waters NOVA PAK C is Column (3.9°-150 mm); eluent A: aqueous $Et_3N$—HOAc (50 mM, pH 7), eluent B: 20% MeCN in A; gradient from 0% B to 50% B in 30 min; flow: preparative: 5 mL/min, analytical: 0.5 mL/min.

Example 20

Determination of the physical properties of 6-amino-5-nitro-3-(1'-beta-D-2'-deoxyribofuranosyl)-2(1H)-pyridone The pKa The pH of an aqueous solution (30 mL) of as 6-amino-5-nitro-3-(1'-beta-D-2'-deoxyribofuranosyl)-2(1H)-pyridone (ca. 0.5 mg; 2 μmol) was varied by subsequent additions of various amounts of dilute aqueous HCl or NaOH, and UV scans (220-500 nm) were taken at every pH. UV spectrum for the deprotonated form (at pH 11): $\lambda_{max}$=402 nm, extinction coefficient=22600 $M^{-1}cm^{-1}$. For the protonated form (at pH 3): $\lambda_{max}$=382 nm, extinction coefficient=21400 $M^{-1}cm^{-1}$. The $pK_a$ was determined by plotting the pH versus the quotient of absorption at two different wavelengths (e.g. 410 nm/360 nm or 270 nm/290 nm).

Measurement of the Epimerization Rate of 4.

For the epimerization rate at high pH, 4 (1 mg; 4 μmol) was dissolved in water (5 mL) and the pH adjusted to 11.0 by the addition of aqueous NaOH (2 M; 20 μL). The solution was incubated at 23 (±1)° C. After certain time intervals, an aliquot (500 μL) was removed, neutralized with aqueous $Et_3N$—HOAc buffer (1 M; pH 7; 0.5 mL) and analyzed by analytical rp-HPLC. The epimerization rate at low pH was determined by dissolving 4 (19 mg; 70 mmol) in water (10 mL), partitioning the resulting solution into 4 aliquots and setting the pH of each of them to a given value (2.0, 3.0, 4.1 and 5.0, respectively) by addition of dilute aqueous HCl (0.1-1 M; 10-50 μL). These solutions were incubated at 37 (±1.5)° C. After given time intervals, aliquots of 200 μL were removed, neutralized with aqueous $Et_3N$—HOAc buffer (200 mM; pH 7; 0.8 mL) and analyzed by analytical rp-HPLC. The peak corresponding to starting material 4 was integrated. The fraction of 4 after time t was calculated as f=(end)+(1-end) exp(-kt), with the value for "end" being determined to be 0.09 from the reaction at pH 2.0 after 14 days.

What is claimed is:

1. A nucleoside analog selected from the group consisting of

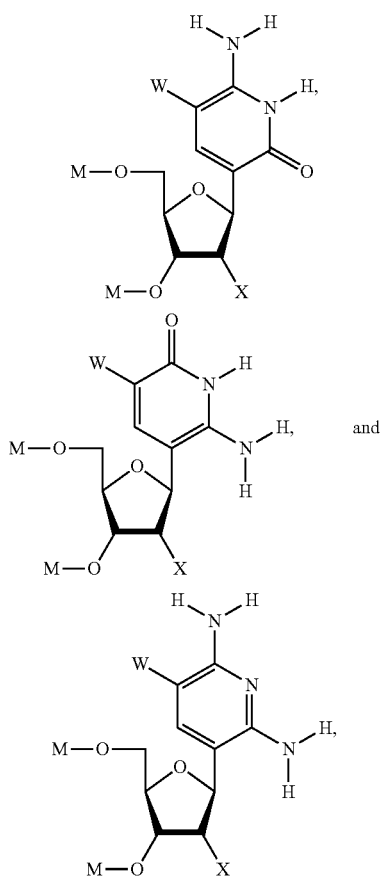

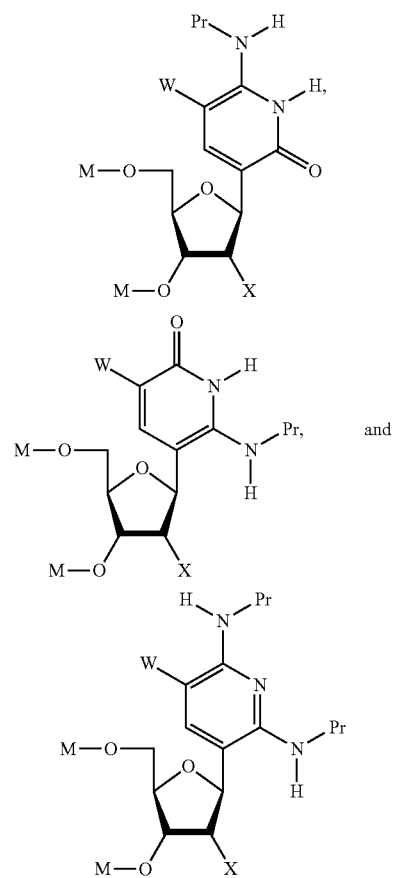

wherein X is independently selected from the group consisting of —H, —OH, —O-Me, —O-allyl, and —O-alkyl, M is independently selected from the group consisting of —H, —PO₃H₂, —P₂O₆H₃, —P₃O₉H₄ and —PO₂H(OR)—, and W is an electron withdrawing group independently selected from the group consisting of —NO₂, —CN, —COOR', and —CONHR', wherein R is independently selected from the group consisting of —H, alkyl, and aryl, and R' is selected from the group consisting of alkyl, aryl, a fluorescent moiety, and a moiety that binds to a metal ion.

2. A process for the synthesis of an oligonucleotide, wherein said process comprises contacting an oligonucleotide primer with an oligonucleotide template and incubating the resulting template-primer complex with a DNA polymerase, RNA polymerase, or reverse transcriptase in the presence of a 5'-triphosphate of the analog in claim 1.

3. The nucleoside analog of claim 1, wherein W is nitro.

4. The nucleoside analog of claim 1, wherein W is cyano.

5. A process for the synthesis of an oligonucleotide comprising incubating an oligonucleotide with terminal transferase in the presence of a 5'-triphosphate of the analog of claim 1.

6. A nucleoside analog and protected phosphoramidites thereof selected from the group consisting of wherein X is independently selected from the group consisting of —H, O—Pr, O-Me, O-allyl, and O-alkyl, M is independently selected from the group consisting of trityl, acetyl, methoxytrityl, dimethoxytrityl, and —P—(NR₂)O-beta-cyanoethyl, and W is an electron withdrawing group independently selected from the group consisting of NO₂, —CN, —COOR', and —CONHR', wherein R' is selected from the group consisting of alkyl, aryl, a fluorescent moiety and a moiety that binds to a metal ion, and Pr is a protecting moiety independently selected from the group consisting of acyl and formamidinyl.

7. The nucleoside analog and protected phosphoramidites thereof of claim 6, wherein W is nitro.

8. The nucleoside analog and protected phosphoramidites thereof of claim 6, wherein W is cyano.

9. An oligonucleotide comprising a sequence of nucleoside units wherein at least one of the nucleoside units is replaced by a nucleoside analog selected from the group consisting of

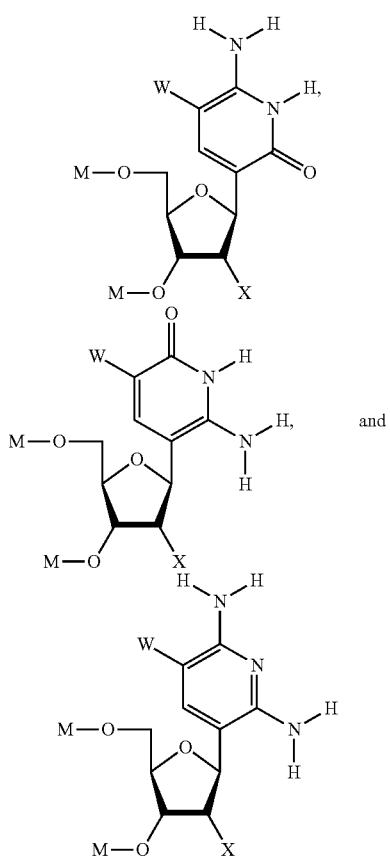 and wherein X is H, OH, O-methyl, O-allyl, or O-alkyl, M denotes the points of attachment to the oligonucleotide chain, and W is an electron withdrawing group independently selected from the group consisting of $-NO_2$, $-CN$, $-COOR'$, and $-CONHR'$, wherein R' is selected from the group consisting of alkyl, aryl, a fluorescent moiety and a moiety that binds to a metal ion.

10. A solid support comprising an oligonucleotide sequence according to claim 9 attached to a solid support.

11. The solid support according to claim 10, wherein said solid support is a bead.

12. The solid support according to claim 10, wherein said support is a two dimensional array.

13. The solid support according to claim 10, wherein said support is a one dimensional array.

14. A fluorescently labeled oligonucleotide sequence comprising the oligonucleotide sequence according to claim 9, attached to a substituent that can be activated with electromagnetic radiation to fluoresce and a second substituent that quenches fluorescence emission.

15. The oligonucleotide sequence of claim 9, wherein W is nitro.

16. The oligonucleotide sequence of claim 9, wherein W is cyano.

* * * * *

UNITED STATES PATENT AND TRADEMARK OFFICE
CERTIFICATE OF CORRECTION

| | | |
|---|---|---|
| PATENT NO. | : 8,053,212 B1 | Page 1 of 1 |
| APPLICATION NO. | : 11/372400 | |
| DATED | : November 8, 2011 | |
| INVENTOR(S) | : Steven Albert Benner | |

It is certified that error appears in the above-identified patent and that said Letters Patent is hereby corrected as shown below:

Column 18,
Line 2, "IICl (cone)" should read --HCl (conc)--.

Column 21,
Line 17, "(0.2μ a cellulose" should read --(0.2 μ cellulose--.

Column 25,
Line 42, "1.0 M, 8.0)" should read --1.0 M, pH 8.0)--.

Column 28,
Lines 14-15, "Waters NOVA PAK C is Column" should read --Waters NOVA PAK $C_{18}$ Column--.

Signed and Sealed this
Sixth Day of March, 2012

David J. Kappos
*Director of the United States Patent and Trademark Office*

SEQUENCE LISTING

<160> NUMBER OF SEQ ID NOS: 5

<210> SEQ ID NO 1
<211> LENGTH: 31
<212> TYPE: DNA

```
<213> ORGANISM: Artificial Sequence
<220> FEATURE:
<221> NAME/KEY: misc_feature
<222> LOCATION: (1)..(1)
<223> OTHER INFORMATION: a nonstandard nucleotide of the instant
      invention
<220> FEATURE:
<222> LOCATION: (3)..(3)
<223> OTHER INFORMATION: a nonstandard nucleotide of the instant
      invention
<220> FEATURE:
<222> LOCATION: (4)..(4)
<223> OTHER INFORMATION: a nonstandard nucleotide of the instant
      invention
<220> FEATURE:
<222> LOCATION: (5)..(5)
<223> OTHER INFORMATION: a nonstandard nucleotide of the instant
      invention
<220> FEATURE:
<222> LOCATION: (27)..(27)
<223> OTHER INFORMATION: a nonstandard nucleotide of the instant
      invention
<220> FEATURE:
<222> LOCATION: (28)..(28)
<223> OTHER INFORMATION: a nonstandard nucleotide of the instant
      invention
<220> FEATURE:
<222> LOCATION: (29)..(29)
<223> OTHER INFORMATION: a nonstandard nucleotide of the instant
      invention
<220> FEATURE:
<222> LOCATION: (31)..(31)
<223> OTHER INFORMATION: a nonstandard nucleotide of the instant
      invention
<220> FEATURE:
<223> OTHER INFORMATION: Synthetic, chemically synthesized

<400> SEQUENCE: 1
ytyyrtgtgt tttctacaag ctgatgyrra r                                 31

<210> SEQ ID NO 2
<211> LENGTH: 26
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: a nonstandard nucleotide of the instant
      invention
<220> FEATURE:
<222> LOCATION: (3)..(3)
<223> OTHER INFORMATION: a nonstandard nucleotide of the instant
      invention
<220> FEATURE:
<222> LOCATION: (4)..(4)
<223> OTHER INFORMATION: a nonstandard nucleotide of the instant
      invention
<220> FEATURE:
<222> LOCATION: (5)..(5)
<223> OTHER INFORMATION: a nonstandard nucleotide of the instant
      invention
<220> FEATURE:
<223> OTHER INFORMATION: Synthetic, chemically synthesized

<400> SEQUENCE: 2
ytyyrtgtgt tttctacaag ctgatg                                       26

<210> SEQ ID NO 3
<211> LENGTH: 34
<212> TYPE: DNA
<213> ORGANISM: Artificial Sequence
<220> FEATURE:
<221> NAME/KEY: misc_feature
<222> LOCATION: (30)..(30)
<223> OTHER INFORMATION: a nonstandard nucleotide of the instant
      invention
```

```
<220> FEATURE:
<222> LOCATION: (31)..(31)
<223> OTHER INFORMATION: a nonstandard nucleotide of the instant
      invention
<220> FEATURE:
<222> LOCATION: (32)..(32)
<223> OTHER INFORMATION: a nonstandard nucleotide of the instant
      invention
<220> FEATURE:
<222> LOCATION: (34)..(34)
<223> OTHER INFORMATION: a nonstandard nucleotide of the instant
      invention
<220> FEATURE:
<223> OTHER INFORMATION: Synthetic, chemically synthesized

<400> SEQUENCE: 3
agaaaaaaca tcagcttgta gaaaacacay rrar                                34

<210> SEQ ID NO 4
<211> LENGTH: 26
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: a nonstandard nucleotide of the instant
      invention
<220> FEATURE:
<222> LOCATION: (3)..(3)
<223> OTHER INFORMATION: a nonstandard nucleotide of the instant
      invention
<220> FEATURE:
<222> LOCATION: (4)..(4)
<223> OTHER INFORMATION: a nonstandard nucleotide of the instant
      invention
<220> FEATURE:
<222> LOCATION: (5)..(5)
<223> OTHER INFORMATION: a nonstandard nucleotide of the instant
      invention
<220> FEATURE:
<223> OTHER INFORMATION: Synthetic, chemically synthesized

<400> SEQUENCE: 4
ytyyrtgtgt tttctacaag ctgatg                                         26

<210> SEQ ID NO 5
<211> LENGTH: 38
<212> TYPE: DNA
<213> ORGANISM: Artificial Sequence
<220> FEATURE:
<221> NAME/KEY: misc_feature
<222> LOCATION: (12)..(12)
<223> OTHER INFORMATION: a nonstandard nucleotide of the instant
      invention
<220> FEATURE:
<222> LOCATION: (13)..(13)
<223> OTHER INFORMATION: a nonstandard nucleotide of the instant
      invention
<220> FEATURE:
<223> OTHER INFORMATION: Synthetic, chemically synthesized

<400> SEQUENCE: 5
tacatgttca gyraaaacat cagcttgtag aaaacaca                            38
```